(12) United States Patent
Garcia Gimenez et al.

(10) Patent No.: US 10,975,435 B2
(45) Date of Patent: Apr. 13, 2021

(54) KIT AND METHOD FOR THE DIAGNOSIS/PROGNOSIS OF IDIOPATHIC SCOLIOSIS

(71) Applicants: CENTRO DE INVESTIGACIÓN BIOMÉDICA EN RED (CIBER), Madrid (ES); HOSPITAL UNIVERSITARIO Y POLITÉCNICO LA FE., Valencia (ES); UNIVERSITAT DE VALÈNCIA, Valencia (ES)

(72) Inventors: Jose Luis Garcia Gimenez, Madrid (ES); Teresa Bas Hermida, Valencia (ES); Federico Vicente Pallardo Calatayud, Valencia (ES); David Hervas Marin, Valencia (ES); Salvador Mena Molla, Valencia (ES)

(73) Assignees: CENTRO DE INVESTIGACIÓN BIOMÉDICA EN RED (CIBER), Madrid (ES); HOSPITAL UNIVERSITARIO Y POLITÉCNICO LA FE, Valencia (ES); UNIVERSITAT DE VALÈNCIA, Valencia (ES)

( * ) Notice: Subject to any disclaimer, the term of this patent is extended or adjusted under 35 U.S.C. 154(b) by 0 days.

(21) Appl. No.: 15/736,735

(22) PCT Filed: Jun. 16, 2016

(86) PCT No.: PCT/EP2016/063935
§ 371 (c)(1),
(2) Date: Dec. 14, 2017

(87) PCT Pub. No.: WO2016/202944
PCT Pub. Date: Dec. 22, 2016

(65) Prior Publication Data
US 2018/0187261 A1 Jul. 5, 2018

(30) Foreign Application Priority Data
Jun. 16, 2015 (EP) .................................... 15382319

(51) Int. Cl.
*C12Q 1/6886* (2018.01)
*C12Q 1/6883* (2018.01)
*C12Q 1/686* (2018.01)

(52) U.S. Cl.
CPC .......... *C12Q 1/6883* (2013.01); *C12Q 1/686* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC .................. C12Q 1/6809; C12Q 1/686; C12Q 2525/207; C12Q 2600/158; C12Q 2600/178
See application file for complete search history.

(56) References Cited

U.S. PATENT DOCUMENTS

2010/0227325 A1* 9/2010 Vilanova ............. C12Q 1/6883
435/6.1

FOREIGN PATENT DOCUMENTS

WO 03/073102 A1 9/2003

OTHER PUBLICATIONS

Garcia-Giménez et al., Circulating miRNAs as diagnostic biomarkers for adolescent idiopathic scoliosis, Scientific Reports, vol. 8:2646, pp. 1-10. (Year: 2018).*
Torres et al., Diagnostic and prognostic significance of nniRNA signatures in tissues and plasma of endometrioid endometrial carcinoma patients, International Journal of Cancer, vol. 132, pp. 1633-1645. (Year: 2013).*
Chevillet et al., Issues and prospects of microRNA-based biomarkers in blood and other body fluids, Molecules, vol. 19, pp. 6080-6105. (Year: 2014).*
Hui et al., Differential miRNAs profile and bioinformatics analyses in bone marrow mesenchymal stem cells from adolescent idiopathic scoliosis patients, The Spine Journal, vol. 19, pp. 1584-1596. (Year: 2019).*
Zhang et al., Aberrant miR-145-5p/beta-catenin signal impairs osteocyte function in adolescent idiopathic scoliosis, The FASEB Journal, vol. 32, pp. 6537-6549. (Year: 2018).*
Li et al., Plasma microRNAs, miR-223, miR-21 and miR-218, as novel potential biomarkers for gastric cancer detection, PLos ONE, vol. 7, issue 7:e41629, pp. 1-8. (Year: 2012).*
Komatsu et al., Malignant potential in pancreatic neoplasm; new insights provided by circulating miR-223 in plasma, Expert Opinion on Biological Therapy, vol. 15, pp. 773-785. (Year: 2015).*
Gorman et al., "Genetics of Idiopathic Scoliosis," eLS, John Wiley & Sons, Ltd., Chichester, United Kingdom, 6 pages, 2014.
Liu et al., "miR-21 Promotes Human Nucleus Pulposus Cell Proliferation through PTEN/AKT Signaling," *Int. J. Mol. Sci.* 15:4007-4018, 2014.
Qiu et al., "Expressed genes related to adolescent idiopathic scoliosis in spinal facet," *Zhonghua Yixue Zazhi—National Medical Journal of China* 89(33):2328-2333, 2006. (English Abstract Only).
Wang, "Chinese Han Patients With Congenital Scoliosis and Normal Serum Micrornas Contrast Research," Abstract, Doctoral Dissertation posted Feb. 26, 2014, downloaded from https://www.globethesis.com/?t=1224330401455866 on Aug. 21, 2015, 2 pages.
Zheng et al., "Low expression of microRNA-143 is related to degenerative scoliosis possibly by regulation of cyclooxygenase-2 expression," *Int J Clin Exp Med* 8(3):4140-4145, 2015.

* cited by examiner

*Primary Examiner* — Dana H Shin
(74) *Attorney, Agent, or Firm* — Seed IP Law Group LLP

(57) ABSTRACT

The present invention provides a method for diagnosing or detecting Idiopathic Scoliosis, in particular AIS, as well as a method for prognosticating this disease in a human subject.

7 Claims, 6 Drawing Sheets
Specification includes a Sequence Listing.

SEQUENCE LISTING

<160> NUMBER OF SEQ ID NOS: 21

<210> SEQ ID NO 1
<211> LENGTH: 22
<212> TYPE: RNA
<213> ORGANISM: Artificial Sequence
<220> FEATURE:
<223> OTHER INFORMATION: hsa-miR-27a-5p
<220> FEATURE:
<221> NAME/KEY: misc_feature
<222> LOCATION: (1)..(22)

<400> SEQUENCE: 1
agggcuuagc ugcuugugag ca                22

```
<210> SEQ ID NO 2
<211> LENGTH: 21
<212> TYPE: RNA
<213> ORGANISM: Artificial Sequence
<220> FEATURE:
<223> OTHER INFORMATION: hsa-miR-142-5p
<220> FEATURE:
<221> NAME/KEY: misc_feature
<222> LOCATION: (1)..(21)

<400> SEQUENCE: 2
cauaaaguag aaagcacuac u                                          21

<210> SEQ ID NO 3
<211> LENGTH: 22
<212> TYPE: RNA
<213> ORGANISM: Artificial Sequence
<220> FEATURE:
<223> OTHER INFORMATION: hsa-miR-223-5p
<220> FEATURE:
<221> NAME/KEY: misc_feature
<222> LOCATION: (1)..(22)

<400> SEQUENCE: 3
cguguauuug acaagcugag uu                                         22

<210> SEQ ID NO 4
<211> LENGTH: 22
<212> TYPE: RNA
<213> ORGANISM: Artificial Sequence
<220> FEATURE:
<223> OTHER INFORMATION: hsa-miR-320b
<220> FEATURE:
<221> NAME/KEY: misc_feature
<222> LOCATION: (1)..(22)

<400> SEQUENCE: 4
aaaagcuggg uugagagggc aa                                         22

<210> SEQ ID NO 5
<211> LENGTH: 26
<212> TYPE: RNA
<213> ORGANISM: Artificial Sequence
<220> FEATURE:
<223> OTHER INFORMATION: hsa-miR-1226-5p
<220> FEATURE:
<221> NAME/KEY: misc_feature
<222> LOCATION: (1)..(26)

<400> SEQUENCE: 5
gugagggcau gcaggccugg augggg                                     26

<210> SEQ ID NO 6
<211> LENGTH: 18
<212> TYPE: RNA
<213> ORGANISM: Artificial Sequence
<220> FEATURE:
<223> OTHER INFORMATION: hsa-miR-1306-3p
<220> FEATURE:
<221> NAME/KEY: misc_feature
<222> LOCATION: (1)..(13)

<400> SEQUENCE: 6
acguuggcuc ugugggug                                              18

<210> SEQ ID NO 7
<211> LENGTH: 21
<212> TYPE: RNA
```

```
<213> ORGANISM: Artificial Sequence
<220> FEATURE:
<223> OTHER INFORMATION: hsa-miR-4523
<220> FEATURE:
<221> NAME/KEY: misc_feature
<222> LOCATION: (1)..(21)

<400> SEQUENCE: 7
gaccgagagg gccucggcug u                                         21

<210> SEQ ID NO 8
<211> LENGTH: 15
<212> TYPE: DNA
<213> ORGANISM: Artificial Sequence
<220> FEATURE:
<223> OTHER INFORMATION: (REGION) FOWARD PRIMER hsa-miR-27a-5p
<220> FEATURE:
<221> NAME/KEY: misc_feature
<222> LOCATION: (1)..(15)

<400> SEQUENCE: 8
agggcttagc tgctt                                                15

<210> SEQ ID NO 9
<211> LENGTH: 11
<212> TYPE: DNA
<213> ORGANISM: Artificial Sequence
<220> FEATURE:
<223> OTHER INFORMATION: Minimal seq forward primer hsa-miR-27a-5p
<220> FEATURE:
<221> NAME/KEY: misc_feature
<222> LOCATION: (1)..(11)

<400> SEQUENCE: 9
gggcttagct g                                                    11

<210> SEQ ID NO 10
<211> LENGTH: 15
<212> TYPE: DNA
<213> ORGANISM: Artificial Sequence
<220> FEATURE:
<223> OTHER INFORMATION: (Region) forward primer hsa-miR-142-5p
<220> FEATURE:
<221> NAME/KEY: misc_feature
<222> LOCATION: (1)..(15)

<400> SEQUENCE: 10
cataaagtag aaagc                                                15

<210> SEQ ID NO 11
<211> LENGTH: 12
<212> TYPE: DNA
<213> ORGANISM: Artificial Sequence
<220> FEATURE:
<223> OTHER INFORMATION: Minimal sequence forward primer hsa-miR-142-5p
<220> FEATURE:
<221> NAME/KEY: misc_feature
<222> LOCATION: (1)..(12)

<400> SEQUENCE: 11
cataaagtag aa                                                   12

<210> SEQ ID NO 12
<211> LENGTH: 16
<212> TYPE: DNA
<213> ORGANISM: Artificial Sequence
<220> FEATURE:
<223> OTHER INFORMATION: (Region) forward primer hsa-miR-223-5p
<220> FEATURE:
```

-continued

```
<221> NAME/KEY: misc_feature
<222> LOCATION: (1)..(16)

<400> SEQUENCE: 12
cgtgtatttg acaagc                                                          16

<210> SEQ ID NO 13
<211> LENGTH: 12
<212> TYPE: DNA
<213> ORGANISM: Artificial Sequence
<220> FEATURE:
<223> OTHER INFORMATION: Minimal sequence, forward primer hsa-miR-223-5p
<220> FEATURE:
<221> NAME/KEY: misc_feature
<222> LOCATION: (1)..(12)

<400> SEQUENCE: 13
cgtgtatttg ac                                                              12

<210> SEQ ID NO 14
<211> LENGTH: 16
<212> TYPE: DNA
<213> ORGANISM: Artificial Sequence
<220> FEATURE:
<223> OTHER INFORMATION: (Region) forward primer hsa-miR-320b
<220> FEATURE:
<221> NAME/KEY: misc_feature
<222> LOCATION: (1)..(16)

<400> SEQUENCE: 14
aaaagctggg ttgaga                                                          16

<210> SEQ ID NO 15
<211> LENGTH: 12
<212> TYPE: DNA
<213> ORGANISM: Artificial Sequence
<220> FEATURE:
<223> OTHER INFORMATION: Minimal sequence, forward primer hsa-miR-320b
<220> FEATURE:
<221> NAME/KEY: misc_feature
<222> LOCATION: (1)..(12)

<400> SEQUENCE: 15
aaaagctggg tt                                                              12

<210> SEQ ID NO 16
<211> LENGTH: 14
<212> TYPE: DNA
<213> ORGANISM: Artificial Sequence
<220> FEATURE:
<223> OTHER INFORMATION: (Region) forward primer hsa-miR-1226-5p
<220> FEATURE:
<221> NAME/KEY: misc_feature
<222> LOCATION: (1)..(14)

<400> SEQUENCE: 16
gagggcatgc aggc                                                            14

<210> SEQ ID NO 17
<211> LENGTH: 13
<212> TYPE: DNA
<213> ORGANISM: Artificial Sequence
<220> FEATURE:
<223> OTHER INFORMATION: (Region) forward primer hsa-miR-1306-3p
<220> FEATURE:
<221> NAME/KEY: misc_feature
<222> LOCATION: (1)..(13)

<400> SEQUENCE: 17
```

-continued acgttggctc tgg                                                      13

<210> SEQ ID NO 18
<211> LENGTH: 12
<212> TYPE: DNA
<213> ORGANISM: Artificial Sequence
<220> FEATURE:
<223> OTHER INFORMATION: Minimal sequence, forward primer hsa-miR-1306-
      3p
<220> FEATURE:
<221> NAME/KEY: misc_feature
<222> LOCATION: (1)..(12)

<400> SEQUENCE: 18
acgttggctc tg                                                       12

<210> SEQ ID NO 19
<211> LENGTH: 16
<212> TYPE: DNA
<213> ORGANISM: Artificial Sequence
<220> FEATURE:
<223> OTHER INFORMATION: (Region) forward primer hsa-miR-4523
<220> FEATURE:
<221> NAME/KEY: misc_feature
<222> LOCATION: (1)..(16)

<400> SEQUENCE: 19
gaccgagagg gcctcg                                                   16

<210> SEQ ID NO 20
<211> LENGTH: 23
<212> TYPE: RNA
<213> ORGANISM: Artificial Sequence
<220> FEATURE:
<223> OTHER INFORMATION: hsa-miR-671-5p
<220> FEATURE:
<221> NAME/KEY: misc_feature
<222> LOCATION: (1)..(23)

<400> SEQUENCE: 20
aggaagcccu ggaggggcug gag                                           23

<210> SEQ ID NO 21
<211> LENGTH: 22
<212> TYPE: RNA
<213> ORGANISM: Artificial Sequence
<220> FEATURE:
<223> OTHER INFORMATION: has-miR-122-5p
<220> FEATURE:
<221> NAME/KEY: misc_feature
<222> LOCATION: (1)..(22)

<400> SEQUENCE: 21
uggaguguga caaugguguu ug                                            22

KIT AND METHOD FOR THE DIAGNOSIS/PROGNOSIS OF IDIOPATHIC SCOLIOSIS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200274_401USPC_SEQUENCE_LISTING.txt. The text file is 5.6 KB, was created on Dec. 13, 2017, and is being submitted electronically via EFS-Web.

TECHNICAL FIELD OF THE INVENTION

The present invention relates in general to the field of Adolescent Idiopathic Scoliosis (AIS) detection and prognosis, and more particularly, to plasma circulating microRNAs for the detection/prognosis of AIS.

BACKGROUND OF THE INVENTION

Without limiting the scope of the invention, its background is described in connection with Adolescent Idiopathic Scoliosis (AIS).

Spinal deformities, scoliosis in particular, represent the most prevalent type of orthopaedic deformities in children and adolescents. Idiopathic scoliosis represents the most common form of scoliosis (70-80% of scoliosis diagnosed in adolescents are idiopathic). Adolescent Idiopathic Scoliosis (AIS; OMIM 181800) is a 3D deformity of the spine that causes a coronal imbalance of up to 10 degrees. It affects 2-4% of under-18 population worldwide, which makes it the most common spinal deformity in this stage (Konieczny M R, Senyurt H, Krauspe R. Epidemiology of adolescent idiopathic scoliosis. J Child Orthop. 2013 February; 7(1):3-9). AIS affects mainly female individuals (about 85%) (Lonstein J. E. Adolescent idiopathic scoliosis. The Lancet. 1994; 344: 1407-1412). There is a predominance of females among the severe cases, despite the ratio between men and women being 1:1 in minor curves. However, female to male ratio increases substantially with age. In particular, the prevalence of curves with higher Cobb angles (>40°) in female rises 7.2:1 (Konieczny M R, Senyurt H, Krauspe R. Epidemiology of adolescent idiopathic scoliosis. J Child Orthop. 2013 February; 7(1):3-9). Clinically it is characterized by pain, aesthetic deformity and alterations in pulmonary functions. Genetic and Epigenetics (environmental interactions, life style, gravity, and nutrition) contribute to this disease, so the diagnostic and prognostic of AIS makes the clinical decisions a challenge (Burwell R. G., Dangerfiel P. H., Moulton, A., Grivas T. B. Adolescent idiopathic scoliosis (AIS), environment, exposome and epigenetics: a molecular perspective of postnatal normal spin growth and the etiopathogenesis of AIS with consideration of a network approach and possible implications for medical therapy. Scoliosis 0.2011, 6:26). Patients are aware that their life is exacerbated by many unknowns, and treatments are often ineffective, invasive, and costly. Scoliosis patients also have increased health risks (cancer, cataracts, skin reddening, etc.) due to frequent X-ray exposure (The National Scoliosis Foundation; www.scoliosis.org/info.php) (Knott, P., et al. SOSORT2012 consensus paper: reducing x-ray exposure in pediatric patients with scoliosis. Scoliosis. 2014; 9:4).

Currently, there is an AIS prognostic test commercialized by Transgenomic Inc., USA (www.scoliscore.com). This test is based on the identification of genetic mutations (53 genetic loci) which provide a long-term susceptibility to develop severe AIS. However, this product is, unfortunately, not useful for the analysis of AIS evolution, since it is based on the analysis of 53 polymorfisms in genes, and the genetic of patients do not change over time. Furthermore, the analysis offered by ScoliScore Test cannot be performed in Clinical Analysis Units in Hospitals, among other reasons, because the samples must be sent to Transgenomic laboratories. In addition, such a test does not alter treatment options avalilable (Julien C., et al. Towards a comprehensive diagnostic assay for scoliosis. Personalized Medicine 2013; 10(1), 97-103).

In order to overcome the above mentioned problems, clinicians require new diagnostic and prognostic tools for AIS to:
- detect Idiopathic Scoliosis, in particular AIS, with the already existing equipment in hospitals, and with none or little specific training for health professionals/customers. Preferably, it should also facilitate early detection and treatment to provide a positive effect on long-term results (as demanded by Scoliosis Patients Europe, scolpat.eu/scoliosis/),
- predict the clinical evolution of AIS patients,
- schedule in a coherent way the visits to the hospital and minimize X-ray explorations,
- decide the best time for initial treatment with braces and spine surgery,
- monitor the positive effects of exercise that sometimes is recommended for AIS patients,
- understand the myriad of factors influencing the predisposition and pathogenesis of AIS, and
- it should also identified risk patients in familial cases of AIS, preparing psychologically the young patients which suffer not only of physical limitations and physiological problems but also aesthetic skeletal deformities.

SUMMARY OF THE INVENTION

The present invention solves the above mentioned problem by providing new epigenetic markers, in particular microRNAs that can contribute to improve the characterization of patients suffering from Idiopathic Scoliosis, in particular from AIS, and is based on a prospective study based on an experimental analysis of the epigenetic profile of AIS.

In particular, the present invention includes a method for diagnosing or detecting Idiopathic Scoliosis, in particular AIS, comprising the steps of: obtaining one or more biological samples from the subject suspected of suffering from Idiopathic Scoliosis, in particular AIS; measuring an expression pattern or level of at least one or the combination of microRNAs selected from hsa-miR-1306-3p, hsa-miR-223-5p, hsa-miR-27a-5p, hsa-miR-122-5p, hsa-miR-320b, hsa-miR-1226-5p, hsa-miR-142-5p and hsa-miR-4523, obtained from the one or more biological samples of the subject; and comparing the overall expression pattern of the at least one or combination of microRNAs from the biological sample of the subject suspected of suffering from Idiopathic Scoliosis, in particular AIS, with the expression pattern of said microRNAs from a biological sample of a normal subject, wherein the normal subject is a healthy subject not suffering from Idiopathic Scoliosis, in particular AIS, and wherein a change in the expression of at least one or the combination of hsa-miR-1306-3p, hsa-miR-223-5p, hsa-miR-27a-5p, hsa-miR-122-5p, hsa-miR-320b, hsa-miR-1226-5p, hsa-miR-142-5p and hsa-miR-4523, is indicative of Idiopathic Scoliosis, in particular AIS.

Preferably, the present invention includes a method for diagnosing or detecting Idiopathic Scoliosis, in particular AIS, comprising the steps of: obtaining one or more biological samples from the subject suspected of suffering from Idiopathic Scoliosis, in particular AIS; measuring an expression pattern or level of at least hsa-miR-223-5p, obtained from the one or more biological samples of the subject; and comparing the expression pattern of at least hsa-miR-223-5p from the biological sample of the subject suspected of suffering from Idiopathic Scoliosis, in particular AIS, with the expression pattern of at least said microRNA from a biological sample of a normal subject, wherein the normal subject is a healthy subject not suffering from Idiopathic Scoliosis, in particular AIS, and wherein a change in the expression of at least hsa-miR-223-5p, is indicative of Idiopathic Scoliosis, in particular AIS.

$$Pr(\text{patient}) = \frac{e^{-7.11+1.50*miR122+1.15*miR27a+6.30*miR223-3.08*miR1306}}{1+e^{-7.11+1.50*miR122+1.15*miR27a+6.30*miR223-3.08*miR1306}}$$

Equation 1. Algorithm for the calculation of the probability of suffering from Adolescent Idiopathic Scoliosis (AIS) in a human subject according the determination of circulating miRNA levels.

Figure 4:
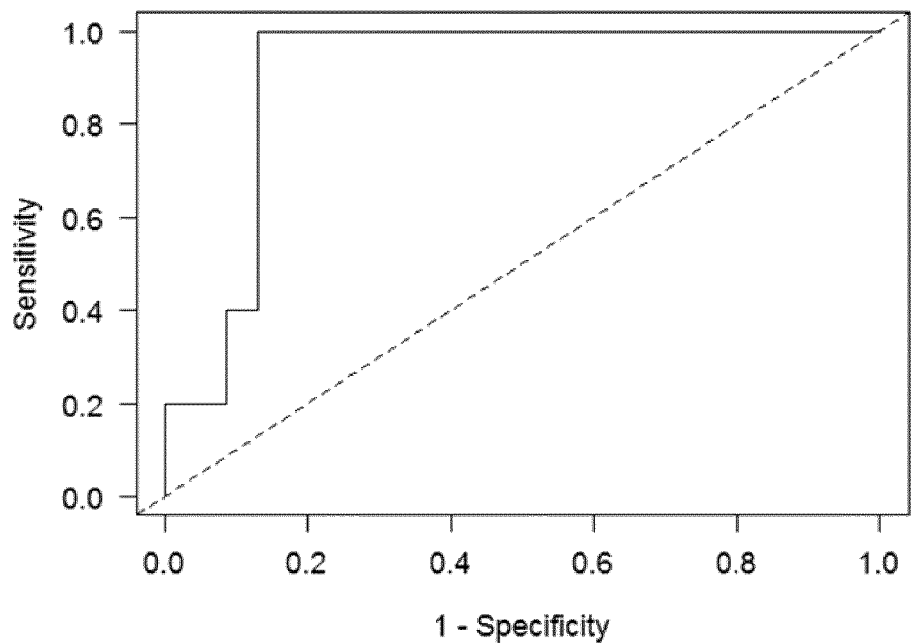

FIG. 4. Receiver operating characteristic curve analysis of the 4-miRNA signature validated by RT-qPCR for high risk of severe curves in AIS. Our model uses a panel of 4-miRNA signature composed by miR-122, miR-27a, miR-223 and miR-1306 achieving an AUC value of 0.90 (CI: 0.79-1). When using the optimal cut-point when considering a 50% of probability of high risk, all 4-miRNAs yielded a sensitivity of 33.3% and specificity of 84.0%.

$$Pr(\text{high risk}) = \frac{e^{-4.44-1.37*miR122-0.26*miR27a+2.50*miR223+1.04*miR1306}}{1+e^{-4.44-1.37*miR122-0.26*miR27a+2.50*miR223+1.04*miR1306}}$$

Equation 2. Algorithm for the calculation of the probability of receiving a bad prognosis associated to high risk curves in Adolescent Idiopathic Scoliosis (AIS) in a human subject according the determination of circulating miRNA levels.

$$Pr(\text{patient}) = \frac{e^{(-0.067+0.05*miR.223+0.03*miR.27a-0.01*miR.320b+0.02*miR.1226+0.03*miR.142-0.58*miR.4523)}}{1+e^{(-0.067+0.05*miR.223+0.03*miR.27a-0.01*miR.320b+0.02*miR.1226+0.03*miR.142-0.58*miR.4523)}}$$

Equation 3: Algorithm for the calculation of the probability of suffering from Adolescent Idiopathic Scoliosis (AIS) in a human subject according the determination of normalized reads values obtained from Small-RNA sequencing data.

Figure 5:
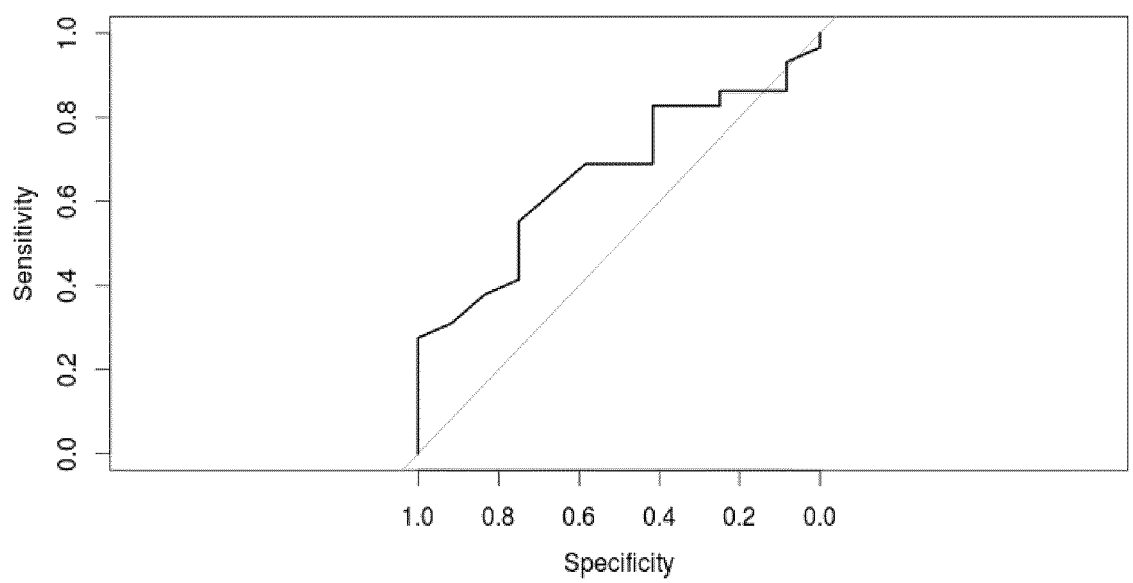

FIG. 5. Receiver operating characteristic curve analysis of miR-122 validated by qRT-qPCR for diagnosing AIS. AUC value of 0.6652 (CI: 0.4923-0.8381).

Figure 6:
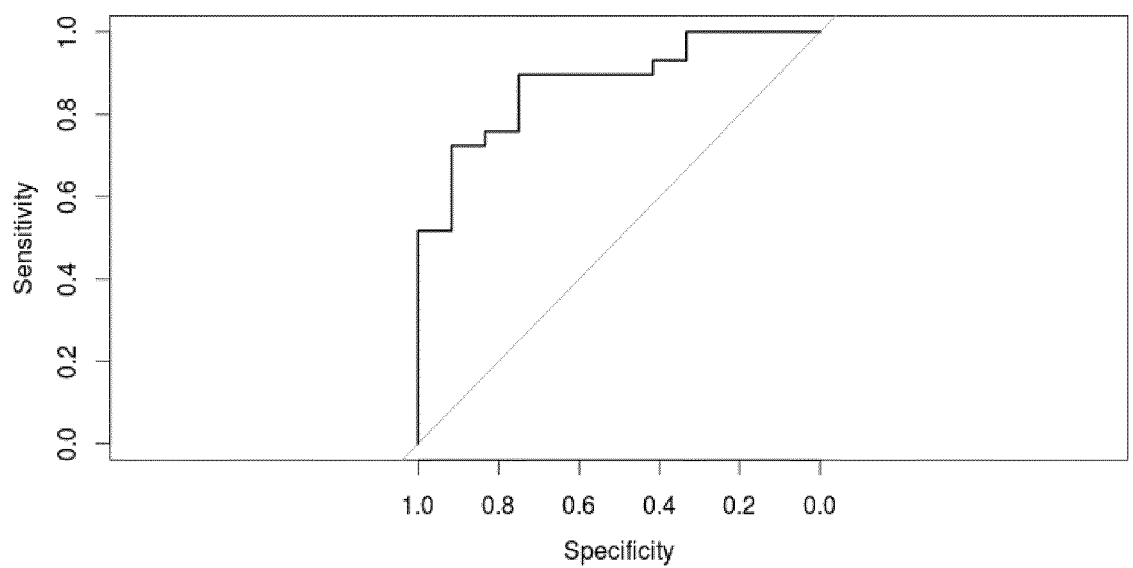

FIG. 6. Receiver operating characteristic curve analysis of miR-223 validated by qRT-qPCR for diagnosing AIS. AUC value of 0.8764 (CI: 0.767-0.9859). Considering the values of sensitivity and specificity obtained during ROC construction, we can get a sensitivity value of 80% and specificity of 75%.

Figure 7:
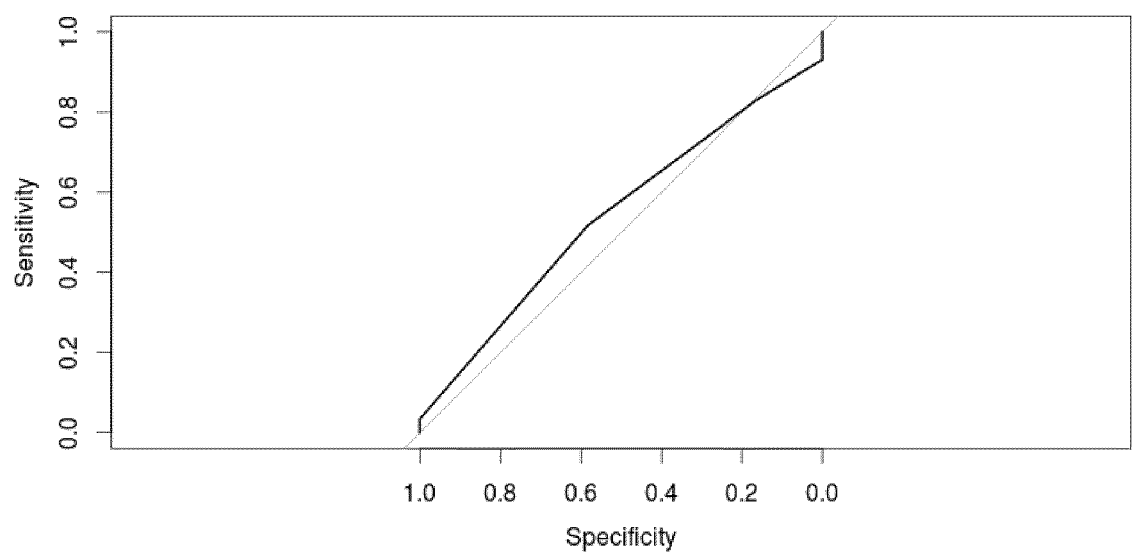

FIG. 7. Receiver operating characteristic curve analysis of miR-1306 validated by qRT-qPCR for diagnosing AIS. AUC value of 0.5417 (CI: 0.3642-0.7191).

Figure 8:
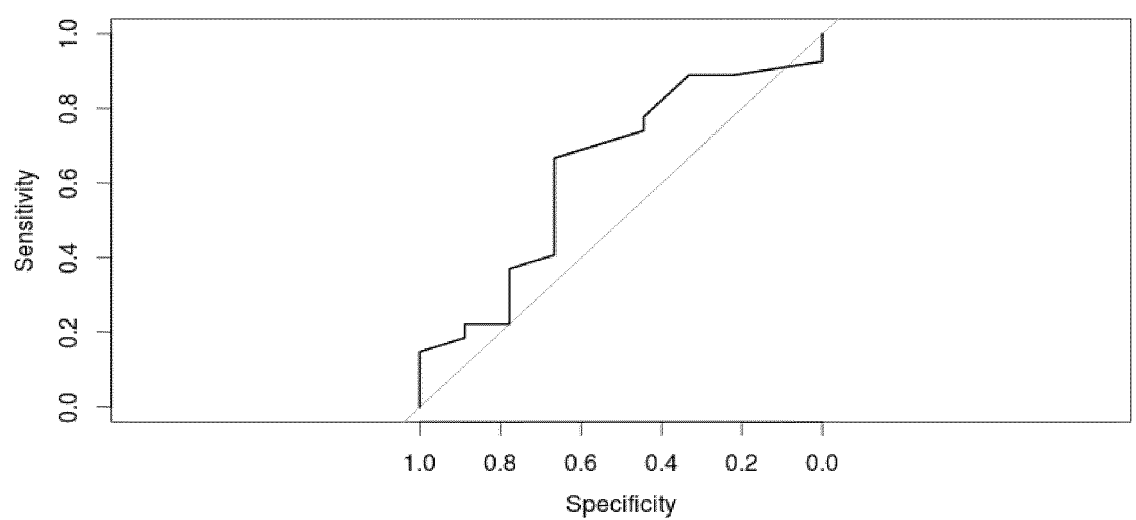

FIG. 8. Receiver operating characteristic curve analysis of miR-27a validated by qRT-qPCR for diagnosing AIS. AUC value of 0.6358 (CI: 0.4132-0.8584).

DETAILED DESCRIPTION OF THE INVENTION

The present invention constitutes the first to report a comprehensive study of circulating miRNAs as biomarkers in AIS patients and healthy controls. Our results demonstrate that circulating miRNAs in plasma can serve as biomarkers for AIS, so providing a new method for diagnosing and prognosticating AIS, thus avoiding repetitive X-ray irradiation for progression monitoring. In this context, the authors of the present invention have found novel bio-signatures of miRNAs significantly differentially represented between AIS patients and controls. Using these selected bio-signatures based on miRNAs differentially represented, AIS patients can be discriminated with high specificity and sensitivity from healthy subjects.

The diagnostic/prognostic method presented herein is based on epigenetics. Epigenetics gene regulation refers to how a specific structural and chemical configuration of chromatin translates into a defined outcome on transcriptional status of genes. In other words, how molecular mechanisms activated by cellular metabolism, the environment, nutrition, and lifestyle modulates the expression of our genes. The above mentioned interventions have a great impact on the epigenetic code of the cells by means of three important mechanisms consisting on DNA methylation, non-coding RNAs (micorRNAs and lncRNAs) and post-translational modification of histones (Handbook of Epigenetics: The New Molecular and Medical Genetics. Ed. Trygve Tollefsbol. Academic Press. Elsevier New York. 2011).

In particular, the present diagnostic/prognostic approach is based on dynamic biomarkers (epigenetics: microRNAs or miRNAs) instead of static biomarkers (genetics: SNPs), the latter of which only offers a static picture of the disease identifying some genetic contributors to the disease. The present invention thus offers a disruptive diagnostic technology compared to conventional diagnostic tests, including DNA testing.

Specifically, the present invention provides new epigenetic markers, in particular microRNAs that can contribute to improve the characterization of patients suffering from Idiopathic Scoliosis, in particular from AIS, and it was first based on a prospective study based on an experimental analysis of the epigenetic profile of AIS. A total of 30 patients and 13 healthy subjects were included in this study and from this group a total of 17 AIS patients and 10 healthy subjects were selected for miRNAs next generation sequencing studies (NGS). To compare the NGS results of the AIS patient samples with the samples from healthy donors a random forest model was computed. Circulating miRNAs from AIS patients showed differential expression patterns compared to controls after statistical analysis. In fact, a signature formed by 6 miRNAs was able to distinguish patients from controls providing molecular information about the role of these miRNAs in this pathology. The random forest model for the signature formed by these 6 miRNAs achieved a cross-validated accuracy of 100% (100% sensitivity and 100% sensibility). Said 6-miRNA bio-signature consisted of the following biomarkers: hsa-miR-671-5p, hsa-miR-1306-3p, hsa-miR-1226-5p, hsa-miR-27a-5p, hsa-miR-223-5p and hsa-miR-122-5p.

MiRNAs hsa-miR-671-5p and hsa-miR-1306-3p were under-expressed in AIS patients and miRNAs hsa-miR-1226-5p and hsa-miR-27a-5p were overexpressed in AIS patients in comparison to healthy individuals. In the case of hsa-miR-223-5p and hsa-miR-122-5p, these were homogenously over-expressed in plasma from patients but their expression was heterogeneous among controls.

In addition, the authors of the present invention validated the above results and realized that a subset from the above bio-signature, namely a bio-signature form by hsa-miR-1306-3p, hsa-miR-223-5p, hsa-miR-27a-5p and hsa-miR-122-5p provided an area under the curve of 0.95, 95% between [0.89, 1] and the sensibility of this test was 92.9% and its specificity was 72.7%.

Lastly, the authors of the present invention have validated the usefulness of the signature form by the 6 miRNAs, and specific subsets of this signature such as the one form by hsa-miR-1306-3p, hsa-miR-223-5p, hsa-miR-27a-5p and hsa-miR-122-5p, to predict the clinical evolution of AIS patients (see examples and FIG. 4).

Once the authors of the present invention validated the above mentioned bio-signatures, they proceeded to perform a small RNA sequencing and logistic regression method. The results obtained from small RNA sequencing data are shown in example 3. On the basis of these results the authors further selected miRNAs: hsa-miR-223-5p, hsa-miR-27a-5p, hsa-miR-1226-5p, hsa-miR-142-5p, all of them were up-regulated in patients compared to the controls and hsa-miR-320b and hsa-miR-4523, down-regulated in patients compared to the controls.

In addition, as shown in example 4, the authors identified hsa-miR-223 as a miRNA able to discriminate by itself cases from controls with an Area under the curve: 0.8764; 95% CI: 0.767-0.9859.

On the basis of these results, the authors construed different models in order to choose the best combinations of miRNAs for AIS diagnosis. For this purpose, the authors selected different combinations of miRNAs from the discovered miRNAs from Small RNA sequencing and logistic regression method ("hsa-miR-27a-5p" "hsa-miR-320b" "hsa-miR-1226-5p" "hsa-miR-142-5p" "hsa-miR-4523" "hsa-miR-223") and/or from those validated by qRT-PCR previously discovered by Small RNA sequencing and random forest method ("hsa-miR-122-5p" "hsa-miR-1306-3p" "hsa-miR-27a-5p" "hsa-miR-223"). Since, "hsa-miR-27a-5p" "hsa-miR-223" were identified in both analysis and hsa-miR-223 was a miRNA capable to discriminate cases from controls by itself with an Area under the curve: 0.8764; 95% CI: 0.767-0.9859, all of the tested combinations analysed comprised miR-223.

A logistic regression model was fitted and the AIC value (Akaike Information Criterion) calculated for each possible combination (2^7=128 combinations). The authors obtained 10 models with the best AIC values. The miRNAs involved in each model were as follows:

1. hsa-miR-223-5p and hsa-miR-1226-5p and hsa-miR-1306-3p;
2. hsa-miR-223-5p and hsa-miR-320b and hsa-miR-4523;
3. hsa-miR-223-5p and hsa-miR-27a-5p and hsa-miR-1306-3p;
4. hsa-miR-223-5p and hsa-miR-142-5p and hsa-miR-1306-3p;
5. hsa-miR-223-5p and hsa-miR-320b and hsa-miR-142-5p;
6. hsa-miR-223-5p and hsa-miR.27a.5p and hsa-miR-1226-5p;
7. hsa-miR-223-5p and hsa-miR-320b and hsa-miR-1226-5p;
8. hsa-miR-223-5p and hsa-miR-4523 and hsa-miR-1306-3p;
9. hsa-miR-223-5p and hsa-miR-1226-5p and hsa-miR-4523;
10. hsa-miR-223-5p and hsa-miR-27a-5p and hsa-miR-20b.

Therefore, in one aspect the present invention includes a method for diagnosing or detecting Idiopathic Scoliosis, in particular AIS, in a human subject comprising the steps of: obtaining one or more biological samples from the subject suspected of suffering from Idiopathic Scoliosis, in particular AIS; measuring an expression pattern or level of at least one or more of the microRNAs selected from the list consisting of hsa-miR-1306-3p, hsa-miR-223-5p, hsa-miR-27a-5p, hsa-miR-122-5p, hsa-miR-320b, hsa-miR-1226-5p, hsa-miR-142-5p and hsa-miR-4523, obtained from the one or more biological samples of the subject; and comparing the expression pattern of the one or more microRNAs from the biological sample of the subject suspected of suffering from Idiopathic Scoliosis, in particular AIS, with the expression pattern of said microRNA/s from a biological sample of a normal subject, wherein the normal subject is a healthy subject not suffering from Idiopathic Scoliosis, in particular AIS, and wherein a change in the expression of any of hsa-miR-1306-3p, hsa-miR-223-5p, hsa-miR-27a-5p, hsamiR-122-5p, hsa-miR-320b, hsa-miR-1226-5p, hsa-miR-142-5p and hsa-miR-4523, is indicative of Idiopathic Scoliosis, in particular AIS.

In one embodiment of this aspect, the present invention includes a method for diagnosing or detecting Adolescent Idiopathic Scoliosis (AIS) in a human subject comprising the steps of: obtaining one or more biological samples from the subject suspected of suffering from Idiopathic Scoliosis, in particular AIS; measuring an expression pattern or level of at least hsa-miR-223-5p, obtained from the one or more biological samples of the subject; and comparing the expression pattern of said microRNA from the one or more biological samples of the subject suspected of suffering from Idiopathic Scoliosis, in particular AIS, with the expression pattern of said microRNA from a biological sample of a normal subject, wherein the normal subject is a healthy subject not suffering from Idiopathic Scoliosis, in particular AIS, and wherein a change in the expression of hsa-miR-223-5p, is indicative of Idiopathic Scoliosis, in particular AIS. Preferably, wherein overexpression or overrepresentation of hsa-miR-223-5p, is indicative of Idiopathic Scoliosis, in particular AIS.

In one embodiment of this aspect, the present invention includes a method for diagnosing or detecting Adolescent Idiopathic Scoliosis (AIS) in a human subject comprising the steps of: obtaining one or more biological samples from the subject suspected of suffering from Idiopathic Scoliosis, in particular AIS; measuring an expression pattern or level of at least the microRNAs selected from the list consisting of any of the following combinations of miRNAs:

hsa-miR-223-5p, hsa-miR-1226-5p and hsa-miR-1306-3p;
hsa-miR-223-5p, hsa-miR-320b and hsa-miR-4523;
hsa-miR-223-5p, hsa-miR-27a-5p and hsa-miR-1306-3p;
hsa-miR-223-5p, hsa-miR-142-5p and hsa-miR-1306-3p;
hsa-miR-223-5p, hsa-miR-320b and hsa-miR-142-5p;
hsa-miR-223-5p, hsa-miR-27a-5p and hsa-miR-1226-5p;
hsa-miR-223-5p, hsa-miR-320b and hsa-miR-1226-5p;
hsa-miR-223-5p, hsa-miR-4523 and hsa-miR-1306-3p;
hsa-miR-223-5p, hsa-miR-1226-5p and hsa-miR-4523;
hsa-miR-223-5p, hsa-miR-27a-5p and hsa-miR-320b;

obtained from the one or more biological samples of the subject; and comparing the expression pattern of any of the above combinations of microRNAs from the one or more biological samples of the subject suspected of suffering from Idiopathic Scoliosis, in particular AIS, with the expression pattern of said combination of microRNAs from a biological sample of a normal subject, wherein the normal subject is a healthy subject not suffering from Idiopathic Scoliosis, in particular AIS, and wherein a change in the expression of said combination, is indicative of Idiopathic Scoliosis, in particular AIS.

It is noted that in order to make the above determination of the presence of AIS in a subject, please take into account that hsa-miR-1306-3p, hsa-miR-122-5p, hsa-miR-223-5p, hsa-miR-27a-5p, hsa-miR-1226-5p and hsa-miR-142-5p, all of them were up-regulated in patients compared to the controls, and hsa-miR-320b and hsa-miR-4523, were down-regulated in patients compared to the controls.

In one embodiment of this aspect, the present invention includes a method for diagnosing or detecting Adolescent Idiopathic Scoliosis (AIS) in a human subject comprising the steps of: obtaining one or more biological samples from the subject suspected of suffering from Idiopathic Scoliosis, in particular AIS; measuring an expression pattern or level of at least the microRNAs selected from the list consisting of hsa-miR-1306-3p, hsa-miR-223-5p, hsa-miR-27a-5p and hsa-miR-122-5p, obtained from the one or more biological samples of the subject; and comparing the expression pattern of the combination of microRNAs from the one or more biological sample of the subject suspected of suffering from Idiopathic Scoliosis, in particular AIS, with the expression pattern of said combination of microRNAs from a biological sample of a normal subject, wherein the normal subject is a healthy subject not suffering from Idiopathic Scoliosis, in particular AIS, and wherein a change in the expression of the combination of hsa-miR-1306-3p, hsa-miR-223-5p, hsa-miR-27a-5p and hsa-miR-122-5p is indicative of Idiopathic Scoliosis, in particular AIS.

In one embodiment of this aspect, the present invention includes a method for diagnosing or detecting Adolescent Idiopathic Scoliosis (AIS) in a human subject comprising the steps of: obtaining one or more biological samples from the subject suspected of suffering from Idiopathic Scoliosis, in particular AIS; measuring an expression pattern or level of at least the microRNAs selected from the list consisting of hsa-miR-1306-3p, hsa-miR-223-5p, hsa-miR-27a-5p and hsa-miR-122-5p, obtained from the one or more biological samples of the subject; and comparing the expression pattern of the combination of microRNAs from the one or more biological sample of the subject suspected of suffering from Idiopathic Scoliosis, in particular AIS, with the expression pattern of said combination of microRNAs from a biological sample of a normal subject, wherein the normal subject is a healthy subject not suffering from Idiopathic Scoliosis, in particular AIS, and wherein overexpression or overrepresentation of the combination of hsa-miR-1306-3p, hsa-miR-223-5p, hsa-miR-27a-5p and hsa-miR-122-5p is indicative of Idiopathic Scoliosis, in particular AIS.

Preferably, in this embodiment of the invention, the probability of suffering from Adolescent Idiopathic Scoliosis (AIS) in a human subject according to the method of the invention, by using a plasma sample, is calculated according to the following formula:

$$Pr(\text{patient}) = \frac{e^{-7.11+1.50*miR122+1.15*miR27a+6.30*miR223-3.08*miR1306}}{1+e^{-7.11+1.50*miR122+1.15*miR27a+6.30*miR223-3.08*miR1306}}$$

Figure 2:
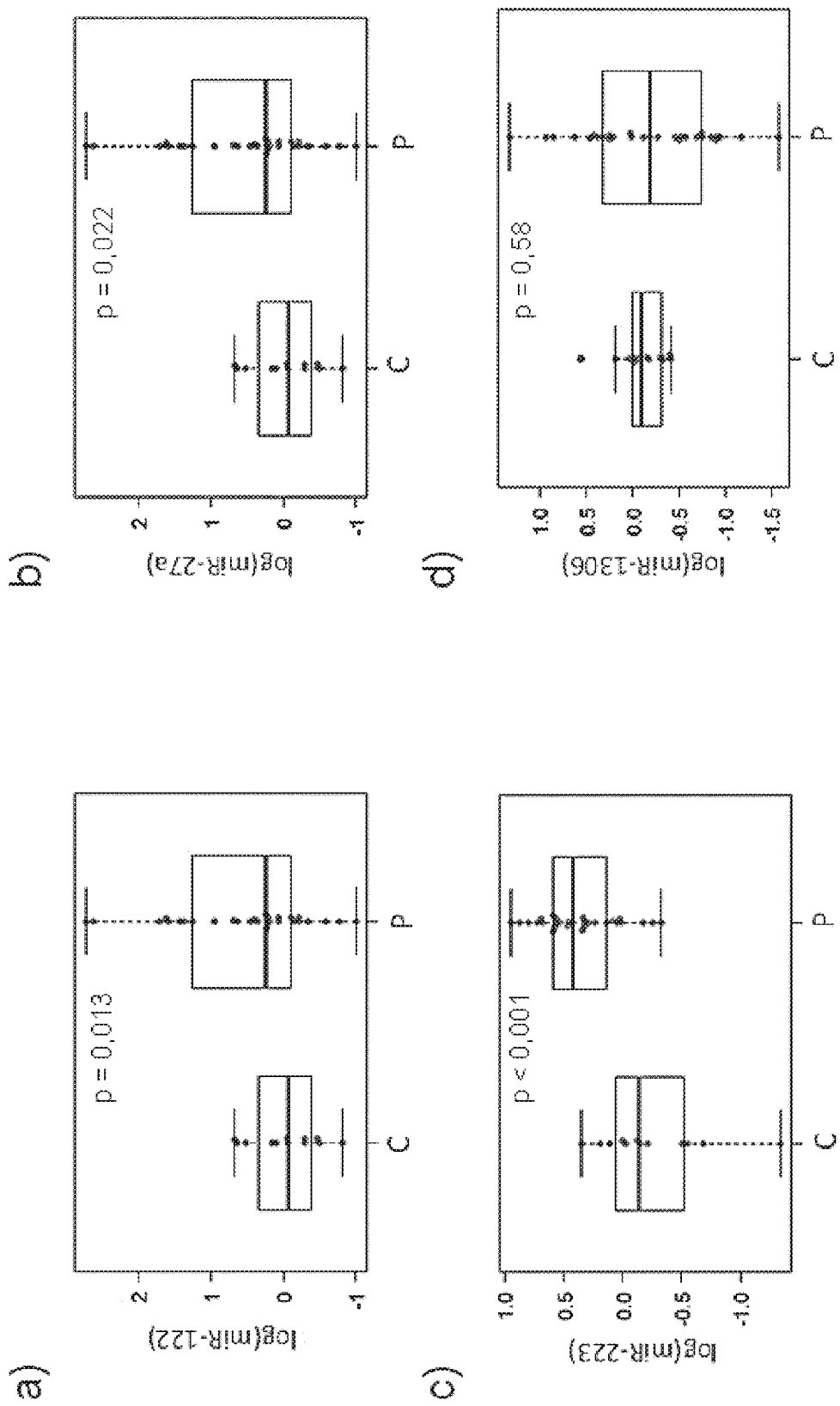
FIG. 2. Relative expression levels of the miRNAs with different representation found in plasma of patients of AIS compared to control healthy subjects. Box plot of relative expression levels of miRNAs analyzed by RT-qPCR normalized to miR-191as endogenous control and calculated using the 2-ΔΔCt method. a) miR-122 (Fold Change, FC=2.5; p<0.05); b) miR-27a (FC=1.75; p<0.05); c) miR-223 (FC=1.75; p<0.001); d) miR-1306 (FC=1.12; p=0.58); and e) miR-671 (FC=0.76; p<0.05). Samples have been ordered according to their corresponding group Controls (C) or AIS patients (P). An independent samples t-test was applied. p<0.05 was considered to indicate a significant difference.
Figure 2:
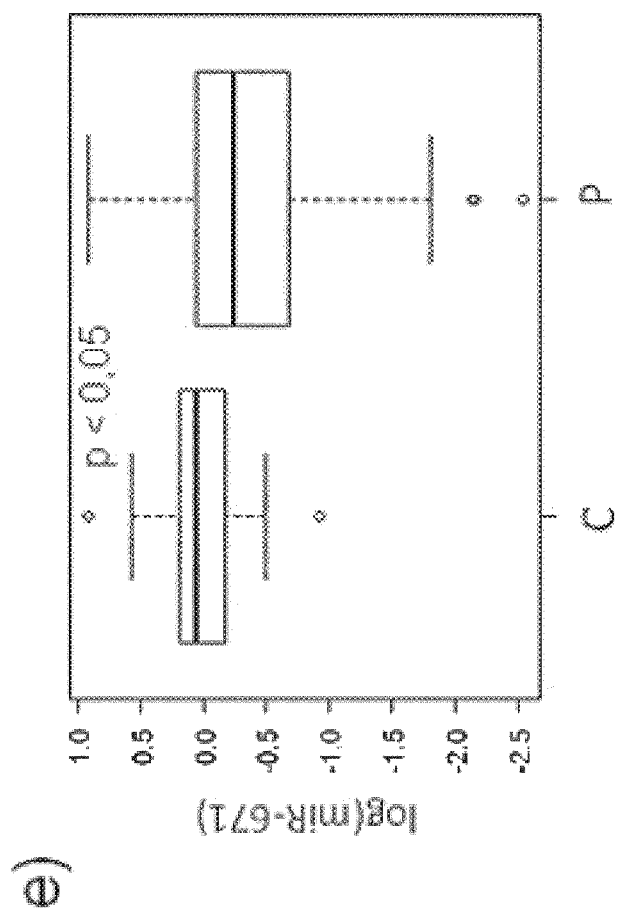

As used herein "overexpression or overrepresentation" of hsa-miR-122-5p, hsa-miR-223-5p, hsa-miR-27a-5p, hsa-miR-1226-5p and hsa-miR-142-5p is understood as an expression greater than 1.5 in the biological sample obtained from a human subject suspected of suffering from Idiopathic Scoliosis, in particular AIS, in comparison to endogen control hsa-miR-191 (see FIG. 2). For those miRNAs analysed by small-RNA sequencing is considered "overexpression or overrepresentation" of hsa-miR-122-5p, hsa-miR-223-5p, hsa-miR-27a-5p, hsa-miR-1226-5p and hsa-miR-142-5p to obtain a FDR<0.5 and positive log FC (logarithm fold change).

As used herein "overexpression or overrepresentation" of hsa-miR-1306-3p, is understood as an expression greater than 1.1 in the biological sample obtained from a human subject suspected of suffering from Idiopathic Scoliosis, in particular AIS, in comparison to endogen control hsa-miR-191 (see FIG. 2).

As used herein "underexpression or underrepresentation" of hsa-miR-671-5p, hsa-miR-320b and hsa-miR-4523 is understood as an expression lower than 0.8 in the biological sample obtained from a human subject suspected of suffering from Idiopathic Scoliosis, in particular AIS, in comparison to endogen control hsa-miR-191 (see FIG. 2). For those miRNAs analysed by small-RNA sequencing is considered "underexpression or underrepresentation" of hsa-miR-671-5p, hsa-miR-320b and hsa-miR-4523 to obtain a FDR<0.5 and negative log FC (logarithm fold change).

As used herein "overexpression or overrepresentation" or "under-expression or under-representation" is preferably determined by microarray expression profiling, PCR, reverse transcriptase PCR, reverse transcriptase real-time PCR, quantitative real-time PCR or sequencing, in particular small-RNA sequencing.

In another embodiment of this aspect of the invention, the method further comprises the analysis of at least one of hsa-miR-671-5p, as compared to expression from the normal subject; preferably, wherein overexpression or over-representation of a combination of hsa-miR-1306-3p, hsa-miR-223-5p, hsa-miR-27a-5p and hsa-miR-122-5p and under-expression or under-representation of hsa-miR-671-5p is indicative of Idiopathic Scoliosis, in particular AIS.

In another embodiment of this aspect of the invention, the one or more biological samples are selected from the group consisting of one or more biological fluids, a plasma sample, a serum sample, a blood sample, a tissue sample, or a faecal sample, preferably a plasma or blood sample.

In another embodiment, the method is capable of detecting early Idiopathic Scoliosis, in particular AIS. In yet another embodiment of this aspect of the invention, the method comprises confidence interval that is 90%, 91%, 92%, 93%, 94%, or 95% of greater.

In another embodiment of this aspect of the invention, the expression level of the microRNAs is measured by microarray expression profiling, PCR, reverse transcriptase PCR, reverse transcriptase real-time PCR, quantitative real-time PCR, end-point PCR, multiplex end-point PCR, cold PCR, droplet digital PCR (ddPCR), ice-cold PCR, mass spectrometry, in situ hybridization (ISH), multiplex in situ hybridization, or nucleic acid sequencing, in particular small-RNA sequencing.

In one further aspect, the present invention includes a method for predicting (prognosticating) the clinical evolution of Idiopathic Scoliosis, in particular AIS, in a human subject comprising the steps of: obtaining one or more biological samples from the subject suffering from Idiopathic Scoliosis, in particular AIS; measuring an expression pattern or level of at least one or more of the microRNAs selected from the list consisting of hsa-miR-1306-3p, hsa-miR-223-5p, hsa-miR-27a-5p, hsa-miR-122-5p, hsa-miR-320b, hsa-miR-1226-5p, hsa-miR-142-5p and hsa-miR-4523, obtained from the one or more biological samples of the subject; and comparing the expression pattern of the one or more microRNAs from the biological sample of the subject suffering from Idiopathic Scoliosis, in particular AIS, with the expression pattern of said microRNA/s from a biological sample of a normal subject, wherein the normal subject is a healthy subject not suffering from Adolescent Idiopathic Scoliosis (AIS), and wherein a change in the expression of at least one or more of hsa-miR-1306-3p, hsa-miR-223-5p, hsa-miR-27a-5p, hsa-miR-122-5p, hsa-miR-320b, hsa-miR-1226-5p, hsa-miR-142-5p and hsa-miR-4523, is indicative of a poor clinical evolution. The term "a poor clinical evolution" is understood as the progress of the disease from mild deformities (between 10 to 25 Cobb angle) to moderate curves (between 25° to 35 Cobb angle) in which patients require bracing, and clinical evolution to severe curves (>45° Cobb angle) so resulting in surgical spine correction of patients.

In one embodiment, the present invention includes a method for predicting (prognosticating) the clinical evolution of Idiopathic Scoliosis, in particular AIS, in a human subject comprising the steps of: obtaining one or more biological samples from the subject suffering from Idiopathic Scoliosis, in particular AIS; measuring an expression pattern or level of at least one or more of the microRNAs selected from the list consisting of hsa-miR-1306-3p, hsa-miR-223-5p, hsa-miR-27a-5p and hsa-miR-122-5p, obtained from the one or more biological samples of the subject; and comparing the expression pattern of the one or more microRNAs from the biological sample of the subject suffering from Idiopathic Scoliosis, in particular AIS, with the expression pattern of said microRNA/s from a biological sample of a normal subject, wherein the normal subject is a healthy subject not suffering from Adolescent Idiopathic Scoliosis (AIS), and wherein overexpression or overrepresentation of at least one or more of hsa-miR-1306-3p, hsa-miR-223-5p, hsa-miR-27a-5p and/or hsa-miR-122-5p is indicative of a poor clinical evolution.

One further embodiment of the present invention includes a method for predicting (prognosticating) the clinical evolution of Idiopathic Scoliosis, in particular AIS, in a human subject comprising the steps of: obtaining one or more biological samples from the subject suffering from Idiopathic Scoliosis, in particular AIS; measuring an expression pattern or level of at least the microRNAs selected from the list consisting of hsa-miR-1306-3p, hsa-miR-223-5p, hsa-miR-27a-5p and hsa-miR-122-5p, obtained from the one or more biological samples of the subject; and comparing the expression pattern of the combination of microRNAs from the one or more biological sample of the subject suffering from Idiopathic Scoliosis, in particular AIS, with the expression pattern of said combination of microRNAs from a biological sample of a normal subject, wherein the normal subject is a healthy subject not suffering from Idiopathic Scoliosis, in particular AIS, and wherein a change in the expression of the combination of hsa-miR-1306-3p, hsa-miR-223-5p, hsa-miR-27a-5p and hsa-miR-122-5p is indicative of a poor clinical evolution.

One further embodiment of the present invention includes a method for predicting (prognosticating) the clinical evolution of Idiopathic Scoliosis, in particular AIS, in a human subject comprising the steps of: obtaining one or more biological samples from the subject suffering from Idiopathic Scoliosis, in particular AIS; measuring an expression pattern or level of at least the microRNAs selected from the list consisting of hsa-miR-1306-3p, hsa-miR-223-5p, hsa-miR-27a-5p and hsa-miR-122-5p, obtained from the one or more biological samples of the subject; and comparing the expression pattern of the combination of microRNAs from the one or more biological sample of the subject suffering from Idiopathic Scoliosis, in particular AIS, with the expression pattern of said combination of microRNAs from a biological sample of a normal subject, wherein the normal subject is a healthy subject not suffering from Idiopathic Scoliosis, in particular AIS, and wherein overexpression or overrepresentation of the combination of has-miR-1306-3p, has-miR-223-5p, has-miR-27a-5p and has-miR-122-5p is indicative of a poor clinical evolution.

Preferably, in this embodiment of the invention, the probability of a receiving a poor clinical evolution according to the method of the invention, by using a plasma sample, is calculated according to the following formula:

$$Pr(\text{high risk}) = \frac{e^{-4.44-1.37*miR122-0.26*miR27a+2.50*miR223+1.04*miR1306}}{1 + e^{-4.44-1.37*miR122-0.26*miR27a+2.50*miR223+1.04*miR1306}}$$

In another embodiment of this aspect of the invention, the method further comprises the analysis of at least one of hsa-miR-671-5p, as compared to expression from the normal subject; preferably wherein overexpression or overrepresentation of a combination of hsa-miR-1306-3p, hsa-miR-223-5p, hsa-miR-27a-5p and hsa-miR-122-5p and under-expression or under-representation of hsa-miR-671-5p is indicative of a poor clinical evolution.

In another embodiment of this aspect of the invention, the one or more biological samples are selected from the group consisting of one or more biological fluids, a plasma sample, a serum sample, a blood sample, a tissue sample, or a fecal sample, preferably a plasma sample. In yet another embodiment of this aspect of the invention, the method comprises confidence interval that is 90%, 91%, 92%, 93%, 94%, or 95% of greater.

In another embodiment of this aspect of the invention, the expression level of the microRNAs is measured by microarray expression profiling, PCR, reverse transcriptase PCR, reverse transcriptase real-time PCR, quantitative real-time PCR, end-point PCR, multiplex end-point PCR, cold PCR, droplet digital PCR (ddPCR), ice-cold PCR, mass spectrometry, in situ hybridization (ISH), multiplex in situ hybridization, or nucleic acid sequencing, in particular small-RNA sequencing.

In another aspect of the invention, the prognostic or diagnostic method of the present invention is used for treating a patient at risk or suffering from Idiopathic Scoliosis, in particular AIS, selecting a suitable therapy for a patient at risk or suffering from Idiopathic Scoliosis, in particular AIS, developing a kit for diagnosis of Idiopathic Scoliosis, in particular AIS, or any combinations thereof. In another aspect, the methods described herein further comprise the step of using the overall expression pattern or level of microRNAs for treatment guidance, or monitoring response to treatment of Idiopathic Scoliosis, in particular AIS. Preferred methods of treatment for patients diagnosed according to the methods of the present invention are braces or surgery. It is very difficult for clinicians to decide the best time for initial treatment with braces or surgery (Cédric Julien K F G, Marie-Yvonne Akoume, Alain Moreau: Towards a Comprehensive Diagnostic Assay for Scoliosis. Personalized Medicine 2013, 10(1):97-103). Furthermore, genetic and phenotypic heterogeneity clearly increases the difficulty of studying complex diseases such as AIS. Therefore, the decision about the best therapies for AIS patients is further complicated.

Prevention of scoliosis could be possible in the near future through tailored pharmacological therapies, which requires the development and validation of pre-symptomatic tests to identify children at risk of developing a scoliosis. Furthermore, physical exercise also showed beneficial effects of this therapeutic intervention in AIS (Bas P, Romagnoli M, Gomez-Cabrera M C, Bas J L, Aura J V, Franco N, Bas T. Beneficial effects of aerobic training in adolescent patients with moderate idiopathic scoliosis. Eur Spine J. 2011 August; 20 Suppl 3:415-9).

Future potential exists in strategies for modulating spinal growth as a means of treating idiopathic scoliosis. This modulation may consist on gene expression regulation or mechanical in nature. As far as we know, there is not any approved drug for idiopathic scoliosis treatment. However, the computational methods used in our analysis using the data obtained from small RNA-sequencing showed that detected miRNAs participate in bone metabolism so linking epigenetics with the etiology of AIS. Our miRNAs target genes involved in the bone metabolism, osteoblastogenesis and osteoclastogenesis. Therefore, the miRNAs described herein could serve to monitor the effect of any future therapy applied to improve AIS, mainly those directed to regulate bone metabolism.

In addition, there are drugs that can affect bone metabolism (i.e. heparin, warfarin, cyclosplorin, glucocorticoids, medroxyprogesterone acetate, thiazide diuretics, and peptide/protein derivatives such as bone morphogenic proteins, etc.) (Wolinsky-Friedland M. Drug-induced metabolic bone disease. Endocrinol Metab Clin North Am 1995; 24:395; Davidge Pitts C J, Kearns A E. Update on medications with adverse skeletal effects. Mayo Clin Proc 2011; 86:338). More recently, it has been proposed the use of melatonin to prevent bone degradation and promote bone formation. Importantly, melatonin can decrease the expression of RANK mRNA (H. Koyama, O. Nakade, Y. Takada, T. Kaku, and K.-H. W. Lau, "Melatonin at pharmacologic doses increases bone mass by suppressing resorption through down-regulation of the RANKL-mediated osteoclast formation and activation," Journal of Bone and Mineral Research, vol. 17, no. 7, pp. 1219-1229, 2002). In addition, melatonin deficiency induces a scoliotic curvature and reduces mean weight and length of cervical vertebrae, possible due to a reduction in the total number of osteocytes (M. Turgut, S. Kaplan, A. T. Turgut, et al., "Morphological, stereological and radiological changes in pinealectomized chicken cervical vertebrae," Journal of Pineal Research, vol. 39, no. 4, pp. 392-399, 2005).

In still another aspect of the invention, if the diagnostic method of the present invention indicates the presence of Idiopathic Scoliosis, in particular AIS, in a subject, said diagnosis can be optionally confirmed by X-ray explorations. In this sense, the current golden standard for AIS diagnosis consist on X-ray explorations. Patients suffering from scoliosis are exposed to an average of 23 radiographs in a period of 3 years (Knott P, Pappo E, Cameron M, Demauroy J, Rivard C, Kotwicki T, Zaina F, Wynne J, Stikeleather L, Bettany-Saltikov J et al: SOSORT 2012 consensus paper: reducing x-ray exposure in pediatric patients with scoliosis. Scoliosis 2014, 9:4). Ronckers et al. followed 5.513 females who were exposed to an average of 23 radiographs during treatment and follow-up of scoliosis and found that the risk of mortality was 46% higher in AIS patients than in the general population, being cancer the primary cause of death in about 23% of the cases (Ronckers C M, Land C E, Miller J S, Stovall M, Lonstein J E, Doody M M: Cancer mortality among women frequently exposed to radiographic examinations for spinal disorders. Radiat Res 2010, 174(1):83-90). In this regard, there is a need for increasing the knowledge in the physiopathological events that take place in AIS and the discovery of molecular biomarkers to generate new accurate and risk-free diagnostic tools (Cédric Julien K F G, Marie-Yvonne Akoume, Alain Moreau: Towards a Comprehensive Diagnostic Assay for Scoliosis. Personalized Medicine 2013, 10(1):97-103). The present invention solves this problem by providing a new series of circulating miRNAs in blood derivatives which can be used for diagnosis of AIS avoiding the recurrent use of X-ray exploration. Using any of the miRNA signatures described herein is possible to avoid repetitive X-ray explorations and only use X-ray radiographs for confirmatory diagnosis and to prepare the surgical intervention.

Yet another aspect of the present invention includes a bio-signature for Idiopathic Scoliosis, in particular AIS, detection or progression, wherein the biomarker comprises at least microRNAs hsa-miR-1306-3p, hsa-miR-223-5p, hsa-miR-27a-5p and hsa-miR-122-5p, or any of the combinations of miRNAs as defined in the first aspect of the invention, and a change in the overall expression of any of the aforesaid combinations of microRNAs in a biological sample obtained from a patient is indicative of Idiopathic Scoliosis, in particular AIS, progression when compared to the overall expression of the aforesaid microRNAs in a biological sample obtained at an earlier time-point from the same patient or indicative of Idiopathic Scoliosis, in particular AIS, detection when compared to the overall expression in a biological sample obtained from a healthy subject.

The skilled artisan will recognize that most often a bio-signature (assay) might include the combination of both over and under-expressed (-represented in biofluids) microRNAs. As such, the present invention also includes in certain embodiments the combination of both over and under-expressed (or represented) microRNAs from respective microRNAs. In particular, the biosignature may include at least one of hsa-miR-671-5p and/or hsa-miR-1226-5p.

Yet another aspect of the present invention includes a kit for diagnosing and/or predicting (prognosticating) idiopathic scoliosis. This kit might comprise the following: (i) PCR primers for quantitatively determining the amount of one or more miRNAs in a biological sample, preferably biological fluids, and more preferably plasma and/or serum. In this sense, the Kit for the diagnosis and/or prognosis of idiopathic scoliosis might comprise the primers and probes necessary for carrying out any of the methodologies described in the previous aspects of the invention.

Merely as an example, two different methods are used for reverse transcription: miRNA-specific or universal reverse transcription. Specifically, in the miRNA-specific approach, miRNAs are reversely transcribed using stem-loop-specific reverse transcription primers. Stem-loop primers designed for a kit useful for the miRNA-specific approach would preferably comprise a region that is complementary to the known sequence on the 3' end of the miRNA, such regions useful as the minimum regions of the stem-loop primers for the kit of the present invention, are illustrated in Table 1 below:

TABLE 1

| | Retrotranscription primer | | |
|---|---|---|---|
| | Sequence | Region | As minimal seq. |
| hsa-miR-27a-5p | AGGGCUUAGCUGC UUGUGAGCA (SEQ ID NO: 1) | TGCTCACA | TGC |
| hsa-miR-142-5p | CAUAAAGUAGAAA GCACUACU (SEQ ID NO: 2) | AGTAGTGC | AGT |
| hsa-miR-223-5p | CGUGUAUUUGACA AGCUGAGUU (SEQ ID NO: 3) | AACTCAGC | AAC |
| hsa-miR-320b | AAAAGCUGGGUUG AGAGGGCAA (SEQ ID NO: 4) | TTGCCCTC | TTG |
| hsa-miR-1226-5p | GUGAGGGCAUGCA GGCCUGGAUGGGG (SEQ ID NO: 5) | CCCCATCC | CCC |

TABLE 1-continued

| | Retrotranscription primer | | |
|---|---|---|---|
| | Sequence | Region | As minimal seq. |
| hsa-miR-1306-3p | ACGUUGGCUCUGG UGGUG (SEQ ID NO: 6) | CACCACCA | CAC |
| hsa-miR-4523 | GACCGAGAGGGCC UCGGCUGU (SEQ ID NO: 7) | ACAGCCGA | ACA |

In addition, the stem-loop primer may contain a short single-stranded, a double-stranded part (the stem), as well as the loop that contains the universal primer-binding sequence. Anyhow, the resulting cDNA is then used as a template for quantitative RT-PCR with 1 miRNA-specific primer, a second universal primer based and a probe of TaqMan PCR technology. Such specific primers useful in the kit of the invention are illustrated in Table 2 below:

TABLE 2

| | Forward Primer | | |
|---|---|---|---|
| | Sequence | Region | As minimal seq. |
| hsa-miR-27a-5p | AGGGCUUAGCUGC UUGUGAGCA (SEQ ID NO: 1) | AGGGCTTAGCTGC TT (SEQ ID NO: 8) | GGGCTTAGCTG (SEQ ID NO: 9) |
| hsa-miR-142-5p | CAUAAAGUAGAAA GCACUACU (SEQ ID NO: 2) | CATAAAGTAGAAA GC (SEQ ID NO: 10) | CATAAAGTAGA A (SEQ ID NO: 11) |
| hsa-miR-223-5p | CGUGUAUUUGACA AGCUGAGUU (SEQ ID NO: 3) | CGTGTATTTGACA AGC (SEQ ID NO: 12) | CGTGTATTTGA C (SEQ ID NO: 13) |
| hsa-miR-320b | AAAAGCUGGGUUG AGAGGGCAA (SEQ ID NO: 4) | AAAAGCTGGGTTG AGA (SEQ ID NO: 14) | AAAAGCTGGGT T (SEQ ID NO: 15) |
| hsa-miR-1226-5p | GUGAGGGCAUGCA GGCCUGGAUGGGG (SEQ ID NO: 5) | GAGGGCATGCAGG C (SEQ ID NO: 16) | GCATGC |
| hsa-miR-1306-3p | ACGUUGGCUCUGG UGGUG (SEQ ID NO: 6) | ACGTTGGCTCTGG (SEQ ID NO: 17) | ACGTTGGCTCT G (SEQ ID NO: 18) |
| hsa-miR-4523 | GACCGAGAGGGCC UCGGCUGU (SEQ ID NO: 7) | GACCGAGAGGGCC TCG (SEQ ID NO: 19) | AGAGGGC |

In one embodiment of this aspect of the invention, miRNAs are retrotranscribed with a universal primer. The 3' ends of miRNAs are elongated with a poly(A) tail or ligated with an universal oligonucleotide and an oligo(dT) or complementary universal oligonucleotide as retrotranscription primer, respectively. Amplification requires a specific primer and a universal primer. Examples of specific primers useful for the kit of the invention are illustrated in Table 3 below

TABLE 3

| | Forward Primer | | |
|---|---|---|---|
| | Sequence | Include | As minimal Seq. |
| hsa-miR-27a-5p | AGGGCUUAGCUGC UUGUGAGCA (SEQ ID NO: 1) | AGGGCTTAGCTGC TT (SEQ ID NO: 8) | GGGCTTAGCTG (SEQ ID NO: 9) |
| hsa-miR-142-5p | CAUAAAGUAGAAA GCACUACU (SEQ ID NO: 2) | CATAAAGTAGAAA GC (SEQ ID NO: 10) | CATAAAGTAGA A (SEQ ID NO: 11) |
| hsa-miR-223-5p | CGUGUAUUUGACA AGCUGAGUU (SEQ ID NO: 3) | CGTGTATTTGACA AGC (SEQ ID NO: 12) | CGTGTATTTGA C (SEQ ID NO: 13) |
| hsa-miR-320b | AAAAGCUGGGUUG AGAGGGCAA (SEQ ID NO: 4) | AAAAGCTGGGTTG AGA (SEQ ID NO: 14) | AAAAGCTGGGT T (SEQ ID NO: 15) |
| hsa-miR-1226-5p | GUGAGGGCAUGCA GGCCUGGAUGGG G (SEQ ID NO: 5) | GAGGGCATGCAGG C (SEQ ID NO: 16) | GCATGC |
| hsa-miR-1306-3p | ACGUUGGCUCUGG UGGUG (SEQ ID NO: 6) | ACGTTGGCTCTGG G (SEQ ID NO: 17) | ACGTTGGCTCT (SEQ ID NO: 18) |
| hsa-miR-4523 | GACCGAGAGGGCC UCGGCUGU (SEQ ID NO: 7) | GACCGAGAGGGCC TCG (SEQ ID NO: 19) | AGAGGGC |

Yet another embodiment of this aspect, the present invention includes a kit for a diagnosis of Idiopathic Scoliosis, in particular AIS, comprising: biomarker detecting reagents (see above as examples of such detecting reagents), preferably primers and probes, for determining a differential expression level of hsa-miR-1306-3p, hsa-miR-223-5p, hsa-miR-27a-5p and hsa-miR-122-5p microRNAs, wherein overexpression or over-representation of a combination of hsa-miR-1306-3p, hsa-miR-223-5p, hsa-miR-27a-5p and hsa-miR-122-5p is indicative of Idiopathic Scoliosis, in particular AIS, wherein a confidence interval for Adolescent Idiopathic Scoliosis (AIS) is 90% or greater.

Yet another embodiment of this aspect, the present invention includes a kit for a diagnosis of Idiopathic Scoliosis, in particular AIS, comprising: biomarker detecting reagents (see above), preferably primers and probes, for determining a differential expression level of hsa-miR-223-5p, or combinations of microRNAs selected from the following list:
  hsa-miR-223-5p, hsa-miR-1226-5p and hsa-miR-1306-3p;
  hsa-miR-223-5p, hsa-miR-320b and hsa-miR-4523;
  hsa-miR-223-5p, hsa-miR-27a-5p and hsa-miR-1306-3p;
  hsa-miR-223-5p, hsa-miR-142-5p and hsa-miR-1306-3p;
  hsa-miR-223-5p, hsa-miR-320b and hsa-miR-142-5p;
  hsa-miR-223-5p, hsa-miR-27a-5p and hsa-miR-1226-5p;
  hsa-miR-223-5p, hsa-miR-320b and hsa-miR-1226-5p;
  hsa-miR-223-5p, hsa-miR-4523 and hsa-miR-1306-3p;
  hsa-miR-223-5p, hsa-miR-1226-5p and hsa-miR-4523;
  hsa-miR-223-5p, hsa-miR-27a-5p and hsa-miR-320b;
  hsa-miR-1306-3p, hsa-miR-223-5p, hsa-miR-27a-5p, hsa-miR-122-5p, hsa-miR-320b, hsa-miR-1226-5p, hsa-miR-142-5p and hsa-miR-4523; or
  hsa-miR-223-5p, hsa-miR-27a-5p, hsa-miR-320b, hsa-miR-1226-5p, hsa-miR-142-5p and hsa-miR-4523;

In one embodiment of this aspect of the invention, the kit further comprises reagents for the detection and analysis of at least one of hsa-miR-671-5p and/or hsa-miR-1226-5p.

In another embodiment, the kit further comprises instructions for use in diagnosing risk for Idiopathic Scoliosis, in particular AIS, wherein the instruction comprise step-by-step directions to compare the expression level of the microRNAs, when measuring the expression of a sample obtained from a subject suspected of having Idiopathic Scoliosis, in particular AIS, with the expression level of a sample obtained from a normal subject, wherein the normal subject is a healthy subject not suffering from Idiopathic Scoliosis, in particular AIS.

In another aspect, the kit further comprises tools, vessels and reagents necessary to obtain samples from a subject selected from the group consisting of one or more biological fluids, a plasma sample, a serum sample, a blood sample, a tissue sample, or a faecal sample, preferably in a plasma sample.

In one further embodiment of this aspect of the invention, the kit comprises biomarker detecting reagents for determining a differential expression level of any of the above mentioned combinations of primers to detect microRNAs, such as pool RT oligonucleotide primers (stem loops) for retrotranscription reaction, dNTPs, reverse transcriptase, buffer, RNase inhibitors and/or nuclease free water for microRNA retrotranscription, and DNA polymerase, dNTPs (without dUTP), fluorescent dye as passive reference, and preferably labelled oligonucleotide primers and probes, and PCR buffers to perform the PCR amplification reaction in a Real-Time PCR system.

Preferably, the kit further comprises an endogen control such hsa-miR-191, which showed to be stable in most sequenced samples.

The kit of the invention may be in the form of a microarray chip, a q-PCR microfluidic card, a q-PCR single tube, q-PCR tubs in a strip or a q-PCR plate (in 96 or 384-well format).

Still, another aspect of the present invention refers to the in vitro use of a kit comprising biomarker detecting reagents for determining the expression level of any of:
  hsa-miR-1306-3p, hsa-miR-223-5p, hsa-miR-27a-5p, hsa-miR-122-5p, hsa-miR-320b, hsa-miR-1226-5p, hsa-miR-142-5p and/or hsa-miR-4523, preferably at least hsa-miR-223-5p;
  hsa-miR-223-5p, hsa-miR-1226-5p and hsa-miR-1306-3p;
  hsa-miR-223-5p, hsa-miR-320b and hsa-miR-4523;
  hsa-miR-223-5p, hsa-miR-27a-5p and hsa-miR-1306-3p;
  hsa-miR-223-5p, hsa-miR-142-5p and hsa-miR-1306-3p;
  hsa-miR-223-5p, hsa-miR-320b and hsa-miR-142-5p;
  hsa-miR-223-5p, hsa-miR-27a-5p and hsa-miR-1226-5p;
  hsa-miR-223-5p, hsa-miR-320b and hsa-miR-1226-5p;
  hsa-miR-223-5p, hsa-miR-4523 and hsa-miR-1306-3p;
  hsa-miR-223-5p, hsa-miR-1226-5p and hsa-miR-4523;
  hsa-miR-223-5p, hsa-miR-27a-5p and hsa-miR-320b; or
  hsa-miR-1306-3p, hsa-miR-223-5p, hsa-miR-27a-5p and hsa-miR-122-5p;
  hsa-miR-1306-3p, hsa-miR-223-5p, hsa-miR-27a-5p, hsa-miR-122-5p, hsa-miR-320b, hsa-miR-1226-5p, hsa-miR-142-5p and hsa-miR-4523; or hsa-miR-223-5p, hsa-miR-27a-5p, hsa-miR-320b, hsa-miR-1226-5p, hsa-miR-142-5p and hsa-miR-4523;

or any combination thereof, for diagnosing or detecting Idiopathic Scoliosis, in particular AIS, and/or predicting (prognosticating) the clinical evolution of Idiopathic Scoliosis, in particular AIS, in a human subject.

In a preferred embodiment of this aspect, the kit for use according to this aspect of the invention is as defined in the previous aspect of the invention.

Further preferred uses of the kit are for treatment guidance, or monitoring response to treatment of Idiopathic Scoliosis, in particular AIS.

Yet another aspect of the present invention includes a computer program suitable for implementing any of the methods of the present invention. In addition, a device comprising the above mentioned computer program also forms part of the present invention as well as its use for the diagnostic/prognostic of Adolescent Idiopathic Scoliosis (AIS) in a human subject.

Finally it is noted that although the diagnostic and prognostic methods described herein are perform by measuring the expression pattern of a bio-signature in an isolated biological sample of a subject and comparing said measurement with the expression pattern of said bio-signature from a biological sample of a normal or healthy subject. Such comparison can also be performed with an already established expression pattern or level, or using normalized and known concentrations of synthetic miRNAs as reference values. Sequence of synthetic miRNAs should contain the consensus sequences of miRNAs described in Table 5.

In addition, it is further noted that a variety of statistical and mathematical methods for establishing the threshold or cutoff level of expression are known in the prior art. A threshold or cutoff expression level for a particular bio-marker may be selected, for example, based on data from Receiver Operating Characteristic (ROC) plots. One of skill in the art will appreciate that these threshold or cutoff expression levels can be varied, for example, by moving along the ROC plot for a particular biomarker or combinations thereof, to obtain different values for sensitivity or specificity thereby affecting overall assay performance. For example, if the objective is to have a robust diagnostic method from a clinical point of view, we should try to have a high sensitivity. However, if the goal is to have a cost-effective method we should try to get a high specificity. The best cutoff refers to the value obtained from the ROC plot for a particular biomarker that produces the best sensitivity and specificity. Sensitivity and specificity values are calculated over the range of thresholds (cutoffs). Thus, the threshold or cutoff values can be selected such that the sensitivity and/or specificity are at least about 70%, and can be, for example, at least 75%, at least 80%, at least 85%, at least 90%, at least 95%, at least 96%, at least 97%, at least 98%, at least 99% or at least 100% in at least 60% of the patient population assayed, or in at least 65%, 70%, 75% or 80% of the patient population assayed.

The present invention is further illustrated by the following examples which merely illustrate the invention and do not limit the same.

EXAMPLES

Example 1. Material and Methods

Study Design and Population

This study is a prospective study based on an experimental analysis of the epigenetic profile of AIS. Patients between 12-18 years old, diagnosed for AIS with a Cobb angle>15° and marked scoliosis, low back pain and no neurologic symptoms.

The inclusion criteria for the patients group were diagnosed for AIS with a Cobb angle>15° and marked scoliosis, minimum follow up for two years, no previous surgical treatment, radiographies available, age between 12-18 years old.

Exclusion criteria were: smoker, active infectious or inflammatory process during extraction, antioxidants intake, neurologic pathology, congenital syndrome pathology, and patients with scoliosis due to secondary causes.

In this study, subjects affected by AIS and healthy subjects were enrolled in the study after ethical committee approval and informed consent signature. Informed consent to create a public sample repository of AIS in the CIBERER Biobank (www.ciberer-biobank.es) were also collected.

Physical and Radiological Explorations

Physical examination consisted on measurement of the following parameters: age, sex, and body mass index (BMI) (Kg/cm2).

A complete neurological exploration including motor and sensory balance, abdominal reflexes, as well as, platellar and Achielles reflexes was performed.

Coronal and Sagittal Balance Evaluation with the Plumb Test.

Vertebral rotation assessment on Adam Test using the Scoliosis Research Society (SRS) scoliometer, and finally, deformity clinical evaluation using the trunk aesthetic clinical evaluation (TRACE) form which consist on shoulder, scapular, thoracic and pelvic asymmetry assessment. Physic evaluation for the control group was the same excluding the TRACE form.

A radiological study was made for all patients included, based on two standing X-rays, anteroposterior and lateral views. It was mandatory to include from skull to pelvis. Risser method was used for skeletal maturity while the Cobb method was used to measure the coronal deformity. On the sagittal plane, they were measured T5-T12 kyphosis (normal values were assigned from 10° to 40°), T12-S1 lordosis (normal values were assigned from 37° to 47°), pelvic incidence (normal values 47°-57°) and pelvic tilt (normal values 9-15). Finally coronal (C7-CSVL lines) and sagittal (C7-S1 lines) balance have been taken into account. According to the SRS criteria, for the present study, it has been considered the diagnosis of scoliosis when the coronal value of the deformity was up to 10 Cobb degrees Classification of the deformity for each patient using The Lenke Classification System for Scoliosis were also collected (Table 4).

TABLE 4

Lenke classification of patients participating in this study

| Lenke | N | % Cohort | Description |
|---|---|---|---|
| 1 | 8 | 60 | Mean Cobb angle 34° (Range 14-80) |
| 2 | 1 | 3.3 | PT curve was 30° and the main thoracic MT curve was 32° |

TABLE 4-continued

Lenke classification of patients participating in this study

| Lenke | N | % Cohort | Description |
|---|---|---|---|
| 3 | 3 | 10 | Mean MT curve was 42.33° while TL/L curve was 33° |
| 4 | 0 | 0 | |
| 5 | 5 | 16.7 | Mean TL/L curve was 26.36ª |
| 6 | 3 | 10 | Mean Cobb angle was 29.6° of MT curve and 38.7° for TL/L curve |

PT: proximal thoracic curve;
MT: Main thoracic curve;
TL/L: thoracolumbar/lumbar curve Finally, all individuals included have completed scoliosis and general health questionnaires, specifically SRS-22, CAVIDRA and SF-36 for patients group and SF-36 for control group.

Since there is no clear explanation for the origin of AIS and simply genetic analysis do not explain completely the physiopathology and prognosis of AIS, we evaluate epigenetic regulators by Next Generation Sequencing.

We purified the miRNAs and analyzed by Next Generation Sequencing the circulating miRNAs from AIS patients (n=17) and healthy subjects (n=10) and by RT-qPCR the miRNAs levels from AIS patients (n=30) and healthy subjects (n=30).

RNA Extraction and Quantification

Blood samples were collected from AIS patients and healthy subjects in EDTA tubes. Each sample was centrifuged at 2500 RPM for 10 minutes to separate the plasma and then stored at −80° C. until RNA extraction. We isolated small RNA from 500 uL of plasma using miRNAeasy kit (Qiagen, Valencia, Calif. USA) according to the manufacturer's protocol. The small RNAs were eluted with 50 µL of RNAse-free water.

The concentration of small RNA was quantified using NanoDrop ND 2000 UV-spectrophotometer (Thermo Scientific, Wilmington, Del., USA).

miRNA Sequencing
Library Preparation cDNA libraries were constructed using Ion Total RNA-Seq Kit v2 from Life Technologies (Cat #4479789) and manufacturers recommended protocol. Purified miRNA samples were run on an microfluidics-based platform Agilent 2100 Bioanalyzer to assess yield and size distribution of the miRNAs. 15 ng of miRNA was hybridized with Ion Adapters in a thermocycler for 10 mins at 65° C. and 5 mins at 30° C. Hybridized miRNA was then incubated for 30 mins. at 30° C. with ligase to ligate the adapters. The hybridized samples were then mixed with a reverse transcriptase master mix and incubated at 42° C. for 30 minutes to generate cDNA libraries. cDNA libraries were purified using Nucleic Acid binding beads, Nucleic Acid buffers and standardized protocol by Life Technologies Ambion (Cat #4479681). The purified cDNA libraries were then amplified by PCR using Platinum PCR Super-Mix High Fidelity and Ion Xpress Barcode reverse and forward primers with the conditions as follows: Step 1: 95° C. for 2 mins; Step 2: 94° C. for 30 sec, 50° C. for 30 sec, 68° C. for 30 sec for 2 cycles; Step 3: 94° C. for 30 sec, 62° C. for 30 sec, 68° C. for 30 sec for 16 cycles; Step 4: 68° C. for 5 mins. The amplified cDNA libraries were purified using Nucleic Acid binding beads, binding buffers and run on Agilent 2100 Bioanalyzer to determine the yield and size distribution of each library.

Templating, Enrichment and Sequencing

Approximately 10 pM of pooled barcoded libraries were used for templating using Life Technologies Ion PI Template OT2 Solutions 200 Kit v3 (Cat #4488318) and manufacturers recommended protocol. Briefly, 10 pM of pool libraries were mixed with Ion PI reagent mix TL, Ion PI PCR reagent B, Ion PI enzyme mix TL and Ion PI Ion sphere particles v3. The mixtures were vortexed, loaded onto an Ion PI Plus reaction filter assembly and fitted onto the Ion OneTouch 2 instrument (Life Technologies). The instrument was turned on and ran for 6.5 hours. After the run, the beads were isolated and quality assessment was performed on Qubid instrument to determine the % of beads that were polyclonal. After polyclonal assessment the samples were enriched using the reagents in the Ion PI Template OT2 Solutions 200 Kit v3 (Cat #4488318), an Ion OneTouch ES instrument and a protocol provided by the manufacturer. After the enrichment the beads were washed and prepared for sequencing. The beads were then loaded onto a pre-prepared and calibrated Ion P1 chip as directed by Life Technologies Ion P1 Sequencing 200 Kit v3 protocol. The loaded chip was then placed into an Ion Proton sequencer and the run was started using a Ion torrent miRNAseq run plan that was configured based on type of library, species, number of run flows required, type of plug-in required, adapter-trimming as well as other parameters specific to the miRNAseq run.

Alignment and Data Analysis

After completion of the proton run, the raw sequences were aligned to the human Hg19 build reference sequence by the Life Technologies Ion Torrent Suite. Aligned BAM files were used for further analysis. BAM files, separated by the specific barcodes, were uploaded to the Strand NGS software (San Francisco, Calif.). Quality control was assessed by the Strand NGS program, which determined the pre- and post-alignment quality of the reads for each sample. The aligned reads were then filtered based on alignment score, match count, mapping quality and average base quality. After filtering, the aligned reads were normalized and quantified using the Deseq algorithm by the Strand NGS program.

Statistical Modeling

First, Deseq normalization was performed on the raw counts data, estimating size factors using the geometric means of transcript counts. After normalization, a variance stabilizing transformation (VST) was applied prior to modeling. We used a random forest algorithm as classifier for our model, and performance of the model was assessed using twenty repetitions of 10-fold cross validation. Biomarker selection was based on variable importance reported by the random forest algorithm using a cutoff value of 0.15 based on a screen plot with all variables ordered from more to less important values. Additionally, we also performed a differential expression analysis based on the negative binomial distribution using the Robinson and Smyth exact negative binomial test and applying a false discovery rate correction to the obtained p-values. Prior to performing the tests, samples were adjusted to an equal effective library size by thinning of the raw counts. All statistical analyses were performed using R software (version 3.1.2) and DESeq2 (version 1.6.3), MLSeq (version 1.2.0) and NBPSeq (version 0.3.0) R-packages.

Real-Time qPCR Validation of a Novel miRNAs Signature from Plasma of AIS Patients and Healthy Controls Reverse transcription reactions were performed using TaqMan miRNA Reverse Transcription kit and miRNA-specific stem-loop primers (Part No. 4366597, Applied Biosystems, Inc) and 100 ng of input cell-free RNA in 15 µL RT reaction. Real-time PCR reactions were performed in triplicate, in scaled-down 10 μL reaction volumes using 5 μL TaqMan 2× Universal PCR Master Mix with No UNG, 0.5 μL TaqMan Small RNA assay (20×) [hsa-miR-122-5p (002245); hsa-miR-27a-5p (002445); hsa-miR-223-5p (002098); hsa-miR-1226-5p (002758); hsa-miR-1306-3p (241056_mat); hsa-miR-671-5p (197646_mat); hsa-miR-191-5p (002299)], 3.5 μL of nuclease free water and 1 μL of RT product. Real-time PCR was carried out on an Applied BioSystems 7900HT thermocycler (Applied Biosystems Inc, Foster City, Calif.) programmed as follows: 50° C. for 2 min, 95° C. for 10 min followed by 45 cycles of 95° C. for 15 s and 60° C. for 1 min. Raw data was analyzed with Expression Suit Software version 1.0.3 (Life Technologies).

Example 2. Results

Clinical Description of AIS Patients

A total of 30 patients and 13 healthy subjects were included in the present research study. In the patients group the mean age was 15.02 year-old (range 12-18). The men-women ratio was 5:1, respectively. IMC mean value on this group was 19.84±3.03. Familiar history was positive on 13 patients, which represent 43.33% of the total group. Mean age at diagnosis was 10.65 year-old (range 8-18). As mentioned previously, the minimum follow up was two years. Mean age at menarche was 12.26 year-old (range 10-15). At the moment of the blood test 2 feminine patients did not yet have the menarche.

From the clinical perspective, the mean TRACE punctuation was 6.6 (range 4-10). The mean coronal plumb test value was 1.18 cm (range 0-2.25). Using a scoliometer, on Adams Test, the mean prominence measured was 6.76° for thoracic trunk and 4.41° for the lumbar segment. Neurologic exploration was normal in all patients.

Attending on radiologic results, the mean skeletal maturity by Risser method was 3.46 (range 1-5). Following the Lenke classification, patients were classified.

On the other hand, mean measures on the sagittal plane were T5-T12 mean kyphosis of 23.06°±11.21 (range 4-42) and T12-S1 mean lordosis of 56.46° 11.10 (range 34-82), while pelvic values were 46.77° as mean pelvic incidence (range 28-64) and 11.2° as mean pelvic tilt (range 1-28) (Table 4). The mean value for radiologic coronal imbalance on the patients group was 1.05 cm (range 0-4.2), while the sagittal imbalance measured on X-ray was −0.15 cm (range −0.88/+0.10). Evaluating scoliosis specific and general health questionnaires showed that the mean punctuation for SRS-22 was 4.12 points (range 2.54-5), 39.64 points on CAVIDRA test (range 21-71) and finally a mean result of 83.56 points (range 39.58-98-05) on SF-36 form.

On the other hand, 13 healthy individuals composed the control group. As mentioned previously, any scoliosis sign was excluded clinically and radiologically.

The mean age on this group was 13.69 year-old (range 12-18). In contrast to the patients group, the men-women ratio was more equilibrated, 1:1.17 respectively. Mean IMC measured was 20.4±2.54 (range 17.17-23.5). Five individuals had positive familiar history of idiopathic scoliosis, which means a 38.46%. Of a total of 6 girls, three of them were still non-menarche.

Physic exploration showed mean coronal plumb test values of 0.26 cm (range 0-2), thoracic hump of 0.7° (range 0-5) while the mean lumbar hump value was 1° (range 0-4). A normal neurologic exploration was objectified in all individuals.

Looking at the X-ray results, the Risser evaluation was 2.46 (range 0-5). On anteroposterior view the mean Cobb angle measured was 2.23° (range 0-8). Sagittal radiologic analysis showed a mean T5-T12 kyphosis of 34.92° (range 18-52) and a mean T12-S1 lordosis of 63.46° (range 40-79). No coronal or sagittal imbalance was detected clinical or radiologically. Pelvic parameters were this time a mean pelvic incidence of 43.92° (range 33-54) and a mean pelvic tilt of 8.8° (range 4.5-15). SF-36 form resulted on a mean punctuation of 85.93 points (72.77-96.8).

A total of 17 AIS patients (age: 15±2 years; IMC: 19.6±2.7 Kg/m2) and 10 healthy subjects (age: 14±2 years; IMC: 20.4±2.5 Kg/m2) were selected for miRNAs Next Generation Sequencing studies. In that case, the mean major curve of patients was 42.8°±18.3 (Cobb's angle), kyphosis was 19.6±10.3, and lordosis was 52.3±12.5 (Table 4). From this series, 7 AIS patients showed an aggressive evolution, while 2 patients showed moderate and 6 patients benign evolution. 2 AIS patients were not defined.

Identification of Differentially Expressed miRNAs by NGS

To compare the NGS results of the AIS patient samples with the samples from healthy donors we first computed a random forest model.

Figure 1:
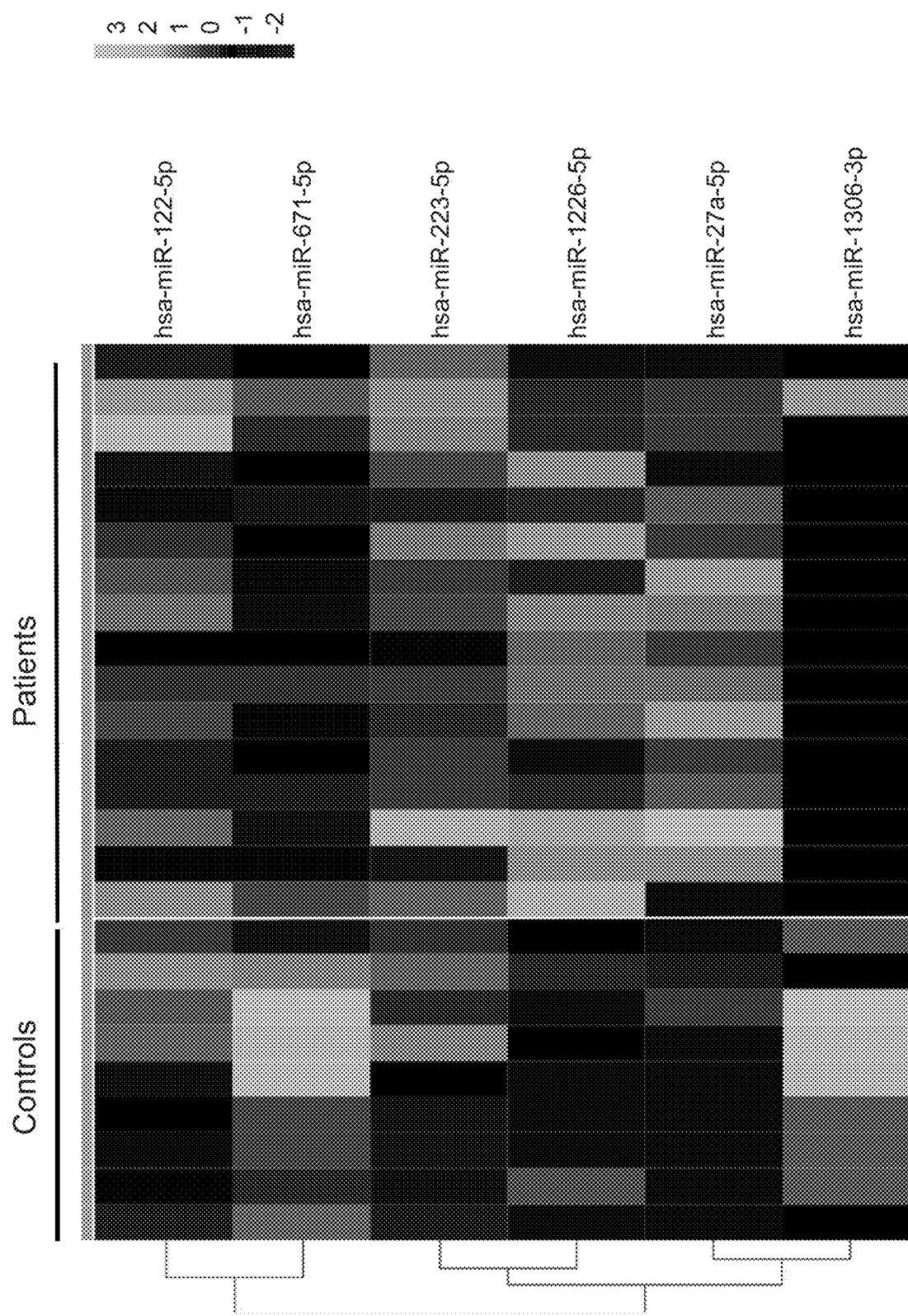
FIG. 1. Heatmap with hierarchical clustering of differentially expressed miRNAs in AIS after NGS analysis. Expression levels of miRNAs selected by the random forest analysis and the Robinson and Smyth test. Raw count values have been log-transformed and samples have been ordered according to their corresponding group Controls (C) or AIS patients (P).

Circulating miRNAs from AIS patients showed differential expression patterns compared to controls after statistical analysis using R. A signature formed by 6 miRNAs was able to distinguish patients from controls providing molecular information about the role of these miRNAs in this pathology. Our random forest model achieved a cross-validated accuracy of 100% (100% sensitivity and 100% sensibility). It selected miR-122-5p, miR-671-5p, miR-223-5p, miR-1226-5p, miR-27a-5p and miR-1306-3p as the most important predictors of the disease. Results of our model are depicted in a heatmap (FIG. 1).

TABLE 5 miRNAs selected as biomarkers for AIS

| miRNA name | Mature sequence | Accesion |
| --- | --- | --- |
| has-miR-671-5p | Aggaagcccugga ggggcuggag (SEQ ID NO: 20) | MIMAT0003880 |
| has-miR-1306-3p | Acguuggcucugg uggug (SEQ ID NO: 6) | MIMAT0005950 |
| has-miR-1226-5p | Gugagggcaugca ggccuggaugggg (SEQ ID NO: 5) | MIMAT0005576 |
| has-miR-27a-5p | Agggcuuagcugc uugugagca (SEQ ID NO: 1) | MIMAT0004501 |
| has-miR-223-5p | Cguguauuugaca agcugaguu (SEQ ID NO: 3) | MIMAT0004570 |
| has-miR-122-5p | uggagugugacaa ugguguuug (SEQ ID NO: 21) | MIMAT0000421 |

From NGS results we detected that miR-671-5p and miR-1306-3p were underexpressed and miR 1226-5p and miR 27a-5p were overexpressed in patients, compared to controls. In the case of miR 223-5p and miR 122-5p, they were homogenously over-represented in plasma from patients but their expression was heterogeneous among controls. Results of the Robinson and Smyth exact negative binomial test reinforced the outcomes of out random forest model, since three of the previously selected miRs showed also a statistically significant differential expression among groups: miR 122-5p (p=0.005), miR 671-5p (p=0.005) and miR 223-5p (p=0.01).

Validation of the miRNA Signature by RT-qPCR

Figure 3:
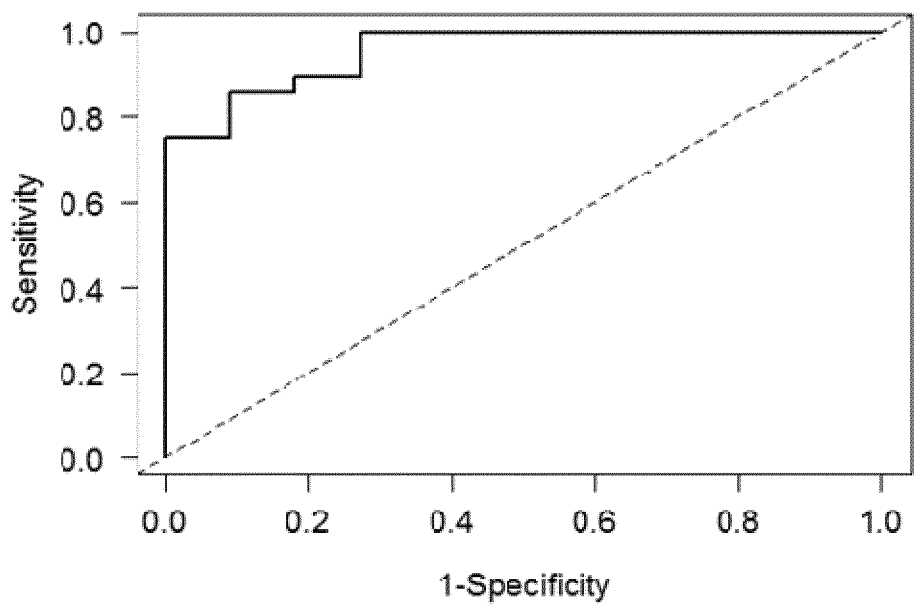
FIG. 3. Receiver operating characteristic curve analysis of the 4-miRNA signature validated by RT-qPCR for diagnosing AIS. Our model uses a panel of 4-miRNA signature composed by miR-122, miR-27a, miR-223 and miR-1306 achieving an AUC value of 0.95 (CI: 0.89-1). When using the optimal cut-point all 4-miRNAs yielded a sensitivity of 92.9% and specificity of 72.7%.

To validate the signature we employed RT-qPCR and included not only additional patients of AIS, but also additional healthy subjects. In total we analyzed the 6-miRNA signature in 60 samples (validation cohort). Through-out this validation study we realized that a subset from the above 6 miRNAs biosignature, namely a biosignature form by hsa-miR-1306-3p, hsa-miR-223-5p, hsa-miR-27a-5p and hsa-miR-122-5p provided an area under the curve of 0.95, 95% between [0.89, 1] and the sensibility of this test was 92.9% and its specificity was 72.7% (as shown in FIG. 3). In addition, this same bio-signature resulted to be adequate to predict the clinical evolution of AIS patients (as shown in FIG. 4).

In fact, FIG. 3 shows a receiver operating characteristic curve analysis of a 4-miRNA signature, validated by RT-qPCR for diagnosing AIS. Our model uses a panel of 4-miRNA signature composed by miR-122, miR-27a, miR-223 and miR-1306 achieving an AUC value of 0.95 (CI: 0.89-1). When using the optimal cut-point all 4-miRNAs yielded a sensitivity of 92.9% and specificity of 72.7%.

$$Pr(\text{patient}) = \frac{e^{-7.11+1.50*miR122+1.15*miR27a+6.30*miR223-3.08*miR1306}}{1+e^{-7.11+1.50*miR122+1.15*miR27a+6.30*miR223-3.08*miR1306}}$$

Equation 1. Algorithm for the calculation of the probability of suffering from Adolescent Idiopathic Scoliosis (AIS) in a human subject according the determination of circulating miRNA levels by using the 4-miRNA signature FIG. 4 shows a receiver operating characteristic curve analysis of the 4-miRNA signature validated by RT-qPCR for high risk of severe curves in AIS. Our model uses a panel of 4-miRNA signature composed by miR-122, miR-27a, miR-223 and miR-1306 achieving an AUC value of 0.90 (CI: 0.79-1). When using the optimal cut-point when considering a 50% of probability of high risk, all 4-miRNAs yielded a sensitivity of 33.3% and specificity of 84.0%.

$$Pr(\text{high risk}) = \frac{e^{-4.44-1.37*miR122-0.26*miR27a+2.50*miR223+1.04*miR1306}}{1+e^{-4.44-1.37*miR122-0.26*miR27a+2.50*miR223+1.04*miR1306}}$$

Equation 2. Algorithm for the calculation of the probability of receiving a bad prognosis associated to high risk curves in Adolescent Idiopathic Scoliosis (AIS) in a human subject according the determination of circulating miRNA levels.

Example 3. Results Obtained from Small RNA Sequencing Data

1. Processing, Aligning and Quantification of the Readings.

There were performed initial quality control checks to know whether the data required filtering to remove ribosomal RNA (rRNA) contamination, if sequence reads required 'trimming' to remove low quality bases and if there was a need to trim reads to remove sequencing adapters. Based on the results obtained, the sequence reads were trimmed to remove sequencing adapters and low quality bases from the 3' end with a Phred-quality threshold less than 20. Finally, the reads with a length less than 18 nucleotides were discarded. A new FastQC run was performed to ensure that the previous quality trimming and/or adapter removal steps successfully conserved high quality reads without being too stringent and without introducing any newly apparent technical biases.

The software used to perform quality control check and the adapters removing/reads filtering were FastQC (www.bioinformatics.babraham.ac.uk/projects/fastqc/) and cutadapt (cutadapt.readthedocs.org/en/stable/), respectively. Once the data was deemed of sufficient quality, all data were mapped against the human Hg38 build reference sequence, taken from UCSC Genome Browser. After mapping, it was performed the intersection between the aligned position of reads and the miRNAs' coordinates taken from miRBase v21. Alignment and quantification steps were performed using the Subread (Liao Y, Smyth G K and Shi W. The Subread aligner: fast, accurate and scalable read mapping by seed-and-vote. Nucleic Acids Research, 41(10):e108, 2013 www.ncbi.nlm.nih.gov/pubmed/23558742) and RSubread (Liao Y, Smyth G K and Shi W. featureCounts: an ecient general-purpose program for assigning sequence reads to genomic features, Bioinformatics, 2013 Nov. 30. www.ncbi.nlm.nih.gov/pubmed/24227677) packages, respectively.

2. Diagnostic Algorithm Analysis from Small-RNA Sequencing Data

It was performed a miRNAs' differential expression analysis between AIS patients and controls. Previously, we filtered out miRNAs with zero counts in any of the samples. Since the smallest group size was 9, we kept miRNAs that achieved at least one count per million (cpm) in at least 9 samples. After that, expression data was normalized using the correction factors approach by means the TMM method (Robinson, M D, and Oshlack, A (2010). A scaling normalization method for differential expression analysis of RNA-seq data. Genome Biology. 2010; 11: R25). We also estimated miRNA-specific dispersions with a quantile-adjusted conditional maximum likelihood (qCML) method (Robinson, M D, and Smyth, G K (2007). Moderated statistical tests for assessing differences in tag abundance. Bioinformatics 23, 2881-2887). Differential expression analysis was performed using the exact test (Robinson, M D, and Smyth, G K (2008). Small sample estimation of negative binomial dispersion, with applications to SAGE data. Biostatistics 9, 321-332).

As result, we obtained 18 deregulated miRNAs (FDR<0.05), 6 were up-regulated and 12 down-regulated in AIS patients compared to the controls. Taking the 11 miRNAs with a FDR<0.01 as variables and the 25 samples as observations, it was fitted a LASSO logistic regression model with binomial distribution (Friedman J., Hastie T., and Tibshirani R., Regularization Paths for Generalized linear models via coordinate Descent. J Statistical Software, 2010; 33(1): 1-22). The most important miRNAs derived from the model were assessed using a leave-one-out cross validation. Those miRNAs which had non-zero coefficients at the value of λ that gave minimum mean cross-validated error, were selected. The selected miRNAs were: hsa-miR-223-5p, hsa-miR-27a-5p, hsa-miR-1226-5p, hsa-miR-142-5p, all of them were up-regulated and hsa-miR-320b, hsa-miR-4523, were down-regulated in patients compared to the controls. The algorithm was calculated using normalized read data with TMM method. The sensibility (Sn), Specificity (Sp) and Area under the Curve (AUC) values obtained using our model were 1 with a confidence interval (CI) of 95%.

$$Pr(\text{patient}) = \frac{e^{(-0.067+0.05*miR.223+0.03*miR.27a-0.01*miR.320b+0.02*miR.1226+0.03*miR.142-0.58*miR.4523)}}{1+e^{(-0.067+0.05*miR.223+0.03*miR.27a-0.01*miR.320b+0.02*miR.1226+0.03*miR.142-0.58*miR.4523)}}$$

Equation 3: Algorithm for the calculation of the probability of suffering from Adolescent Idiopathic Scoliosis (AIS) in a human subject according the determination of normalized reads values obtained from Small-RNA sequencing data.

All statistical analysis were performed using R software (version 3.3.0) and the R packages EdgeR (version 3.12.0), glmnet (version 2.0-2), glmulti (version 1.0.7) y pROC (version 1.8).

Example 4. Cts Normalized Data with miRNAs: miR-122, miR-27a, miR-223 and miR-1306, to Diagnose AIS in Samples from Cases (AIS Samples) and Controls (Healthy Subjects)

1. Sensibility and Specificity of miR-122 to Diagnose AIS in Samples from Cases (AIS Samples) and Controls (Healthy Subjects)

**It was not deemed significant

Coefficients:

|             | Estimate | Std. Error | z value | Pr (>|z|) |
| --- | --- | --- | --- | --- |
| (Intercept) | −0.2194  | 0.6928     | −0.317  | 0.752     |
| miR.122     | 0.7756   | 0.5153     | 1.505   | 0.132     |

The sensibility values for each specificity value are showed below. Although, we calculated the minimum (se. low), maximum (se. high) and median sensibility (se. median) values, we advise to take the median values.

| sp  | se.low | se.median | se.high |
| --- | --- | --- | --- |
| 0.0 | 1.0000 | 1.0000 | 1.0000 |
| 0.1 | 0.7241 | 0.8966 | 1.0000 |
| 0.2 | 0.6552 | 0.8621 | 0.9724 |
| 0.3 | 0.5862 | 0.8276 | 0.9655 |
| 0.4 | 0.5517 | 0.7931 | 0.9311 |
| 0.5 | 0.4828 | 0.7241 | 0.9310 |
| 0.6 | 0.2997 | 0.6483 | 0.8621 |
| 0.7 | 0.2414 | 0.5724 | 0.8276 |
| 0.8 | 0.2068 | 0.4299 | 0.7586 |
| 0.9 | 0.1722 | 0.3483 | 0.6760 |
| 1.0 | 0.1379 | 0.2759 | 0.5517 |

The specificity values for sensibility values are showed below. Although, we calculated the minimum (sp. low), maximum (sp. high) and median specificity (sp. median) values, we advise to take the median values.

| se  | sp.low | sp.median | sp.high |
| --- | --- | --- | --- |
| 0.0 | 1.00000 | 1.00000 | 1.0000 |
| 0.1 | 1.00000 | 1.00000 | 1.0000 |
| 0.2 | 0.80000 | 1.00000 | 1.0000 |
| 0.3 | 0.61920 | 1.00000 | 1.0000 |
| 0.4 | 0.50000 | 0.83330 | 1.0000 |
| 0.5 | 0.41670 | 0.75000 | 1.0000 |
| 0.6 | 0.25000 | 0.66670 | 0.9167 |
| 0.7 | 0.08333 | 0.50000 | 0.8793 |
| 0.8 | 0.00000 | 0.33330 | 0.7500 |
| 0.9 | 0.00000 | 0.08333 | 0.5000 |
| 1.0 | 0.00000 | 0.00000 | 0.1667 |

Area under the curve: 0.6652

95% CI: 0.4923-0.8381 (DeLong) (see FIG. 5)

2. Sensibility and Specificity of miR-223 to Diagnose Cases and Controls.

**It was deemed significant

| sp  | se.low | se.median | se.high |
| --- | --- | --- | --- |
| 0.0 | 1.0000 | 1.0000 | 1.0000 |
| 0.1 | 0.9310 | 1.0000 | 1.0000 |
| 0.2 | 0.8621 | 1.0000 | 1.0000 |
| 0.3 | 0.8276 | 1.0000 | 1.0000 |
| 0.4 | 0.7931 | 0.9655 | 1.0000 |
| 0.5 | 0.7922 | 0.9310 | 1.0000 |
| 0.6 | 0.6552 | 0.8966 | 1.0000 |
| 0.7 | 0.5862 | 0.8621 | 1.0000 |
| 0.8 | 0.4828 | 0.7931 | 0.9655 |
| 0.9 | 0.3793 | 0.7241 | 0.9655 |
| 1.0 | 0.3448 | 0.5862 | 0.8966 |

| se  | sp.low | sp.median | sp.high |
| --- | --- | --- | --- |
| 0.0 | 1.00000 | 1.0000 | 1.0000 |
| 0.1 | 1.00000 | 1.0000 | 1.0000 |
| 0.2 | 1.00000 | 1.0000 | 1.0000 |
| 0.3 | 1.00000 | 1.0000 | 1.0000 |
| 0.4 | 0.83330 | 1.0000 | 1.0000 |
| 0.5 | 0.75000 | 1.0000 | 1.0000 |
| 0.6 | 0.75000 | 0.9167 | 1.0000 |
| 0.7 | 0.58330 | 0.9167 | 1.0000 |
| 0.8 | 0.33330 | 0.7500 | 1.0000 |

| se | sp.low | sp.median | sp.high |
|---|---|---|---|
| 0.9 | 0.16670 | 0.5000 | 0.9167 |
| 1.0 | 0.08333 | 0.3333 | 0.7500 |

Area under the curve: 0.8764

95% CI: 0.767-0.9859 (DeLong) (see FIG. 6)

3. Sensibility and Specificity of miR-1306 to Diagnose Cases and Controls.

**It was not deemed significant

Coefficients:

| | Estimate | Std. Error | z value | Pr (>|z|) |
|---|---|---|---|---|
| (Intercept) | 0.80536 | 0.64215 | 1.254 | 0.210 |
| miR.1306 | 0.07596 | 0.53881 | 0.141 | 0.888 |

| sp | se.low | se.median | se.high |
|---|---|---|---|
| 0.0 | 1.00000 | 1.00000 | 1.0000 |
| 0.1 | 0.67590 | 0.86210 | 0.9655 |
| 0.2 | 0.58620 | 0.80000 | 0.9448 |
| 0.3 | 0.49380 | 0.72780 | 0.9034 |
| 0.4 | 0.40000 | 0.65060 | 0.8648 |
| 0.5 | 0.32510 | 0.57470 | 0.7980 |
| 0.6 | 0.26010 | 0.49030 | 0.7471 |
| 0.7 | 0.20170 | 0.38210 | 0.6759 |
| 0.8 | 0.13790 | 0.26620 | 0.5931 |
| 0.9 | 0.07094 | 0.15170 | 0.3724 |
| 1.0 | 0.00000 | 0.03448 | 0.1034 |

| se | sp.low | sp.median | sp.high |
|---|---|---|---|
| 0.0 | 1.00000 | 1.0000 | 1.0000 |
| 0.1 | 0.85500 | 0.9435 | 1.0000 |
| 0.2 | 0.69230 | 0.8575 | 0.9589 |
| 0.3 | 0.51870 | 0.7708 | 0.9256 |
| 0.4 | 0.37490 | 0.6778 | 0.8926 |
| 0.5 | 0.27680 | 0.5781 | 0.8594 |
| 0.6 | 0.19170 | 0.4667 | 0.7861 |
| 0.7 | 0.07833 | 0.3385 | 0.6606 |
| 0.8 | 0.00000 | 0.2000 | 0.4917 |

| se | sp.low | sp.median | sp.high |
|---|---|---|---|
| 0.9 | 0.00000 | 0.0375 | 0.3402 |
| 1.0 | 0.00000 | 0.0000 | 0.0000 |

Area under the curve: 0.5417

95% CI: 0.3642-0.7191 (DeLong) (see FIG. 7)

4. Sensibility and Specificity of miR-27a to Diagnose Cases and Controls.

**It was not deemed significant

Coefficients:

| | Estimate | Std. Error | z value | Pr (>|z|) |
|---|---|---|---|---|
| (Intercept) | 0.3299 | 0.7294 | 0.452 | 0.651 |
| miR.27a | 0.4782 | 0.4174 | 1.146 | 0.252 |

| sp | se.low | se.median | se.high |
|---|---|---|---|
| 0.0 | 1.00000 | 1.0000 | 1.0000 |
| 0.1 | 0.77780 | 0.9093 | 1.0000 |
| 0.2 | 0.70350 | 0.8889 | 1.0000 |
| 0.3 | 0.60370 | 0.8593 | 1.0000 |
| 0.4 | 0.40740 | 0.8148 | 0.9630 |
| 0.5 | 0.25930 | 0.7407 | 0.9630 |
| 0.6 | 0.14810 | 0.6519 | 0.9259 |
| 0.7 | 0.11110 | 0.4204 | 0.8704 |
| 0.8 | 0.07407 | 0.2593 | 0.8148 |
| 0.9 | 0.05370 | 0.1852 | 0.5640 |
| 1.0 | 0.03704 | 0.1852 | 0.5556 |

| se | sp.low | sp.median | sp.high |
|---|---|---|---|
| 0.0 | 1.0000 | 1.0000 | 1.0000 |
| 0.1 | 0.7667 | 1.0000 | 1.0000 |
| 0.2 | 0.5556 | 0.8889 | 1.0000 |
| 0.3 | 0.4444 | 0.7778 | 1.0000 |
| 0.4 | 0.3333 | 0.7778 | 1.0000 |
| 0.5 | 0.3333 | 0.6667 | 1.0000 |
| 0.6 | 0.2889 | 0.6667 | 0.8889 |
| 0.7 | 0.1926 | 0.5556 | 0.8889 |
| 0.8 | 0.0000 | 0.4444 | 0.7926 |
| 0.9 | 0.0000 | 0.1306 | 0.6667 |
| 1.0 | 0.0000 | 0.0000 | 0.3333 |

Area under the curve: 0.6358

95% CI: 0.4132-0.8584 (DeLong) (see FIG. 8)

The invention claimed is:

1. A method for treating Adolescent Idiopathic Scoliosis (AIS) in a human subject at risk of AIS, the method comprising:
    (i) detecting, by RT-qPCR, an expression level in a test plasma sample from the human subject of each of hsa-miR-1306-3p; hsa-miR-223-5p; hsa-miR-27a-5p; and hsa-miR-122-5p relative, respectively, to the expression level of each of hsa-miR-1306-3p; hsa-miR-223-5p hsa-miR-27a-5p; and hsa-miR-122-5p in a control plasma sample from a healthy subject;
    (ii) determining, from the expression levels of hsa-miR-1306-3p; hsa-miR-223-5p; hsa-miR-27a-5p and hsa-miR-122-5p that are each up-regulated in the test plasma sample relative, respectively, to the expression levels of hsa-miR-1306-3p; hsa-miR-223-5p; hsa-miR-27a-5p; and hsa-miR-122-5p in the control plasma sample, a probability of AIS in the human subject at risk of AIS according to Equation 1:

$$Pr(\text{patient}) = \frac{e^{-7.11+1.50*miR122+1.15*miR27a+6.30*miR223-3.08*miR1306}}{1+e^{-7.11-1.50*miR122+1.15*miR27a+6.30*miR223-3.08*miR1306}},$$

and therefrom identifying the human subject as a human subject in whom AIS is probable; and
    (iii) treating the human subject using one or more of braces; surgery; physical exercise; heparin; warfarin; cyclosporine; glucocorticoids; medroxyprogesterone acetate; thiazide diuretics; melatonin; and a bone morphogenetic protein.

2. The method of claim 1, comprising treating the human subject in whom AIS is probable with one or both of braces and surgery.

3. The method of claim 1, wherein the human subject in whom AIS is probable had previously received an X-ray radiograph.

4. The method claim 3, wherein the human subject in whom AIS is probable had previously received only one X-ray radiograph.

5. The method of claim 1, further comprising, following the determining in (ii) and prior to the treating in (iii), performing an X-ray radiograph on the human subject in whom AIS is probable.

6. The method of claim 1, wherein detecting the expression level of hsa-miR-223-5p comprises use of a forward primer comprising the nucleotide sequence set forth in SEQ ID NO:13.

7. The method of claim 1, wherein:
    a. detecting the expression level of hsa-miR-223-5p comprises use of a forward primer comprising the nucleotide sequence set forth in SEQ ID NO:12 or 13;
    b. detecting the expression level of hsa-miR-1306-3p comprises use of a forward primer comprising the nucleotide sequence set forth in SEQ ID NO:17 or 18; and/or
    c. detecting the expression level of hsa-miR-27a-5p comprises use of a forward primer comprising the nucleotide sequence set forth in SEQ ID NO:8 or 9.

* * * * *

UNITED STATES PATENT AND TRADEMARK OFFICE
CERTIFICATE OF CORRECTION

PATENT NO. : 10,975,435 B2
APPLICATION NO. : 15/736735
DATED : April 13, 2021
INVENTOR(S) : Jose Luis Garcia Gimenez et al.

Page 1 of 1

It is certified that error appears in the above-identified patent and that said Letters Patent is hereby corrected as shown below:

In the Claims

Column 37, Claim 1, Line 30:
"more of" should read: --more of;--.

Column 38, Claim 4, Line 10:
"The method claim 3," should read: --The method of claim 3,--.

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*